United States Patent
Doyle

(10) Patent No.: US 6,613,022 B1
(45) Date of Patent: Sep. 2, 2003

(54) PASSIVE NEEDLE GUARD FOR SYRINGES

(75) Inventor: Mark Christopher Doyle, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 0 days.

(21) Appl. No.: 09/724,657

(22) Filed: Nov. 28, 2000

Related U.S. Application Data

(63) Continuation-in-part of application No. 09/566,224, filed on May 5, 2000.

(51) Int. Cl.$^7$ ................................................ A61M 5/32
(52) U.S. Cl. ...................................................... 604/192
(58) Field of Search ............................ 604/162, 164.08, 604/192, 198, 110, 263, 218, 187, 181, 234, 111, 197

(56) References Cited

U.S. PATENT DOCUMENTS

| | | |
|---|---|---|
| 3,306,290 A | 2/1967 | Weltman |
| 4,767,413 A | 8/1988 | Haber et al. |
| 4,820,275 A | 4/1989 | Haber et al. |
| 4,923,447 A | 5/1990 | Morgan |
| 4,927,416 A | 5/1990 | Tomkiel |
| 4,932,947 A | 6/1990 | Cardwell |
| 4,955,868 A | 9/1990 | Klein |
| 5,059,184 A | 10/1991 | Dyke |
| 5,088,986 A | 2/1992 | Nusbaum |
| 5,176,656 A | 1/1993 | Bayless |
| 5,201,708 A | 4/1993 | Martin |
| 5,201,720 A | 4/1993 | Borgia et al. |
| 5,242,420 A | 9/1993 | Martin |
| 5,273,541 A | 12/1993 | Malenchek |
| 5,433,712 A | 7/1995 | Stiles et al. |
| 5,492,536 A | 2/1996 | Mascia |
| 5,562,624 A * | 10/1996 | Righi et al. ................ 604/110 |
| 5,562,626 A | 10/1996 | Sanpietro |
| 5,573,513 A | 11/1996 | Wozencroft |
| 5,695,475 A | 12/1997 | Best, Jr. et al. |
| 6,159,184 A | 12/2000 | Perez et al. |
| 6,171,283 B1 | 1/2001 | Perez et al. |
| 6,186,980 B1 | 2/2001 | Brunel |
| RE37,439 E | 11/2001 | Firth et al. |
| 6,319,234 B1 | 11/2001 | Restelli et al. |

OTHER PUBLICATIONS

PCT Publication No. WO 00/33900, "Safety Assembly for a Syringe Pre–Filled with Liquid, in Particular a Medicine", Jun. 15, 2001.

EPO Publication No. 0 405 039 A1, "Combine Seringue–Aiguille Auto–Escamotable", Jan. 2, 1991.

(List continued on next page.)

*Primary Examiner*—Brian L. Casler
*Assistant Examiner*—Ann Y Lam
(74) *Attorney, Agent, or Firm*—Orrick, Herrington & Sutcliffe, LLP

(57) ABSTRACT

A passive needle guard includes a body having a cavity therein for receiving a syringe, and a shield. The body is slidable with respect to the shield between retracted and extended positions covering and exposing, respectively, a needle extending from the syringe, the body being biased towards the retracted position. Latch members extend from the shield that include catches for engaging mating catches on the body for holding the body in the extended position. During use, the needle extending from the syringe is inserted into a patient. A plunger is depressed to inject medication from the syringe, thereby deflecting the latch members to disengage the catches and release the body, whereupon the user may controllably retract the body to the retracted position. In the retracted position, cooperating detents on the shield and body engage one another, thereby substantially permanently covering the needle with the shield.

28 Claims, 20 Drawing Sheets

OTHER PUBLICATIONS

PCT Publication No. WO 93/00949 entitled "Single–Shot Disposable Syringe", Jan. 21, 1993.

PCT Publication No. WO 98/35714 entitled "Disposable Safety Syringe", Aug. 20, 1998.

PCT Publication No. WO 99/17823 entitled "Disposable Self–Shielding Unit Dose Syringe Guard", Apr. 15, 1999.

EPO Publication No. 0 680 767 A1 entitled "Non–Reusable Safety Syringe", Nov. 8, 1995.

Robert Malenchek, et al., PCT Publication No. WO 99/32177, "Safety Syringe", Jul. 1, 1999.

Sergio Restelli, et al., PCT Publication No. WO 99/373345, "Disposable Safety Syringe", Jul. 29, 1999.

Mare Brunel, PCT Publication No. WO 00/76565 A1, "Disposable Injection Device", Dec. 21, 2000 (French and English versions).

David C. Medway, PCT Publication No. WO 91/18634, "Hypodermic Needle Protection Device", Dec. 12, 1991.

Thomas C. Kuracina, et al., PCT Publication No. WO 93/17732, "Medical Injection Devices with Safety Features", Sep. 16, 1993.

* cited by examiner

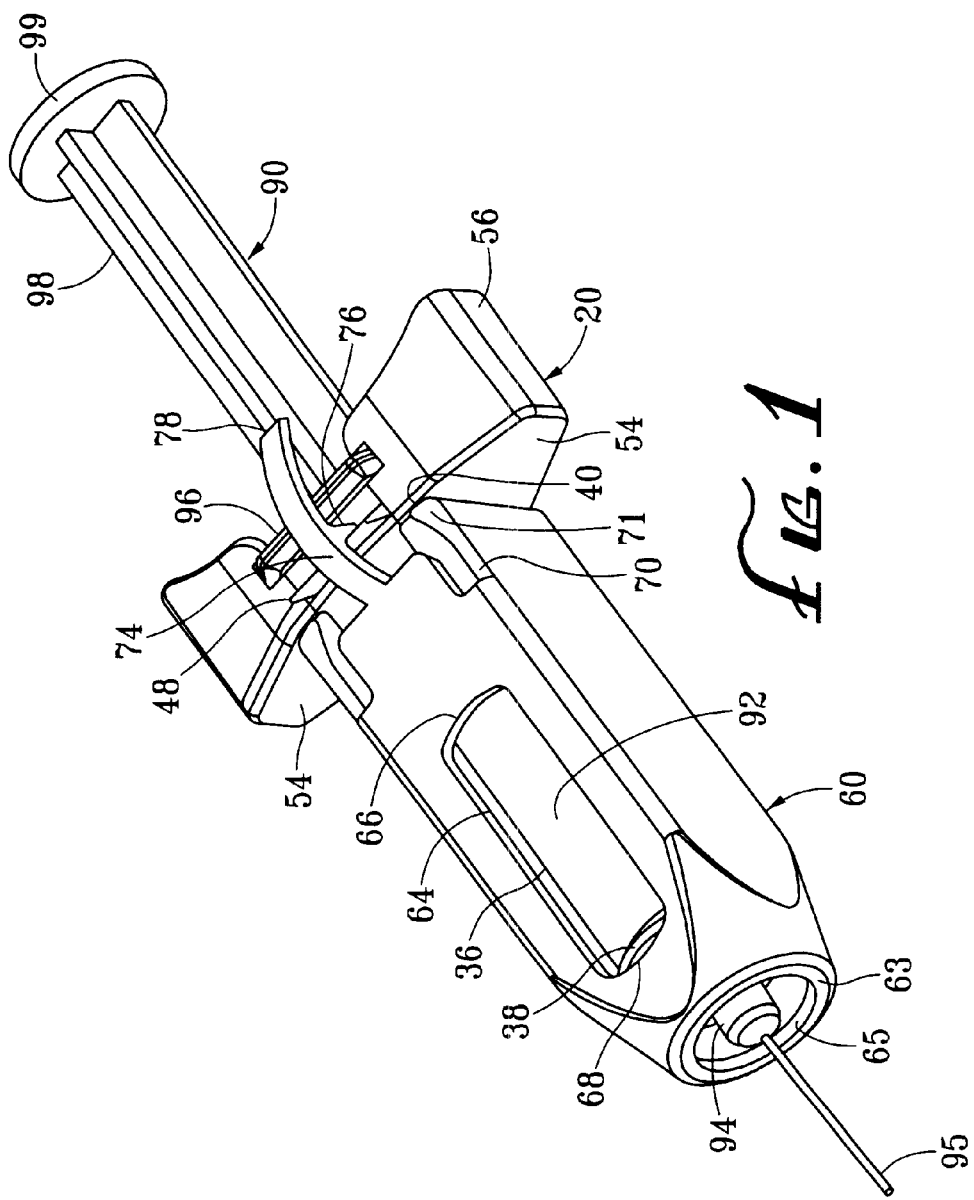

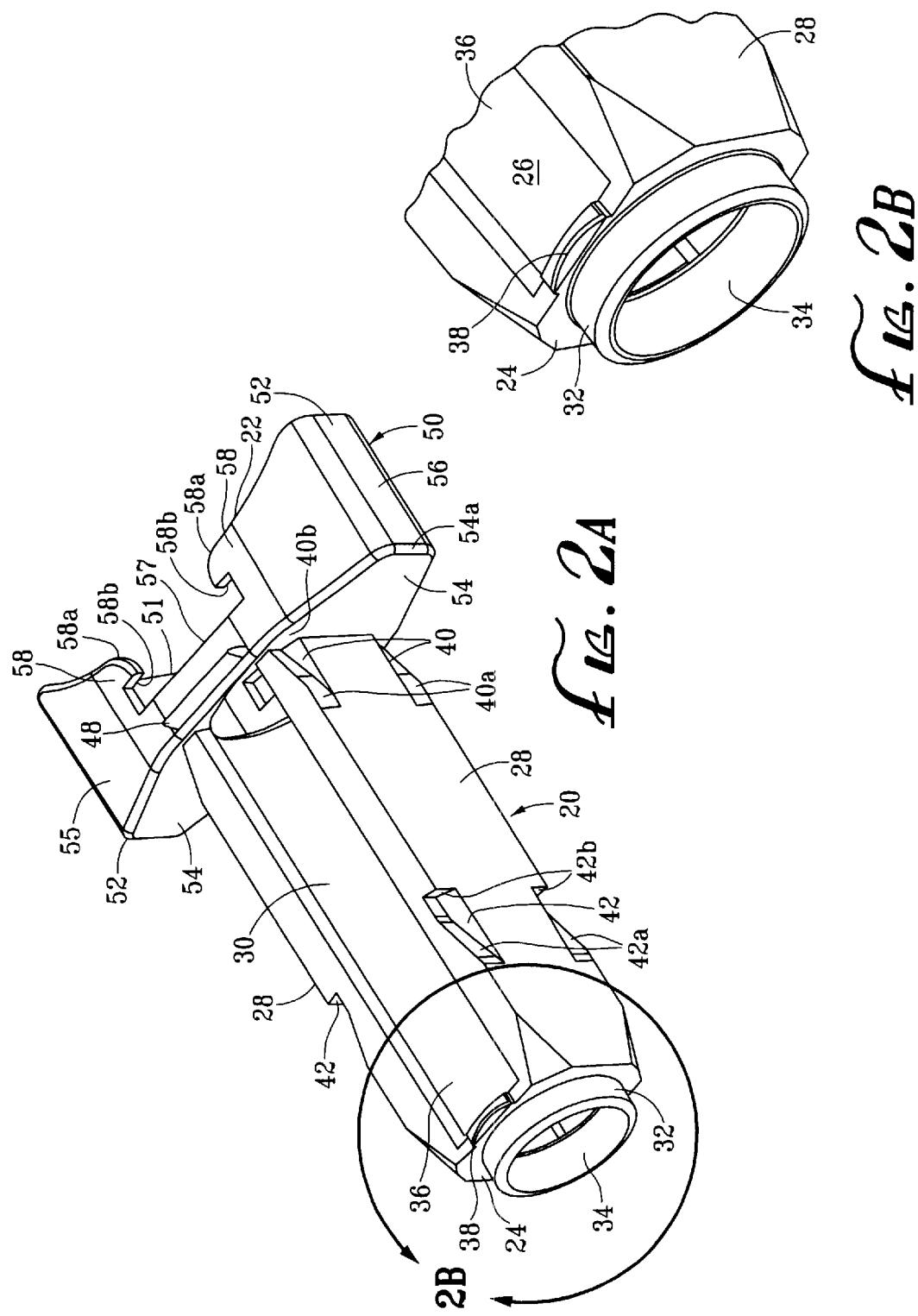

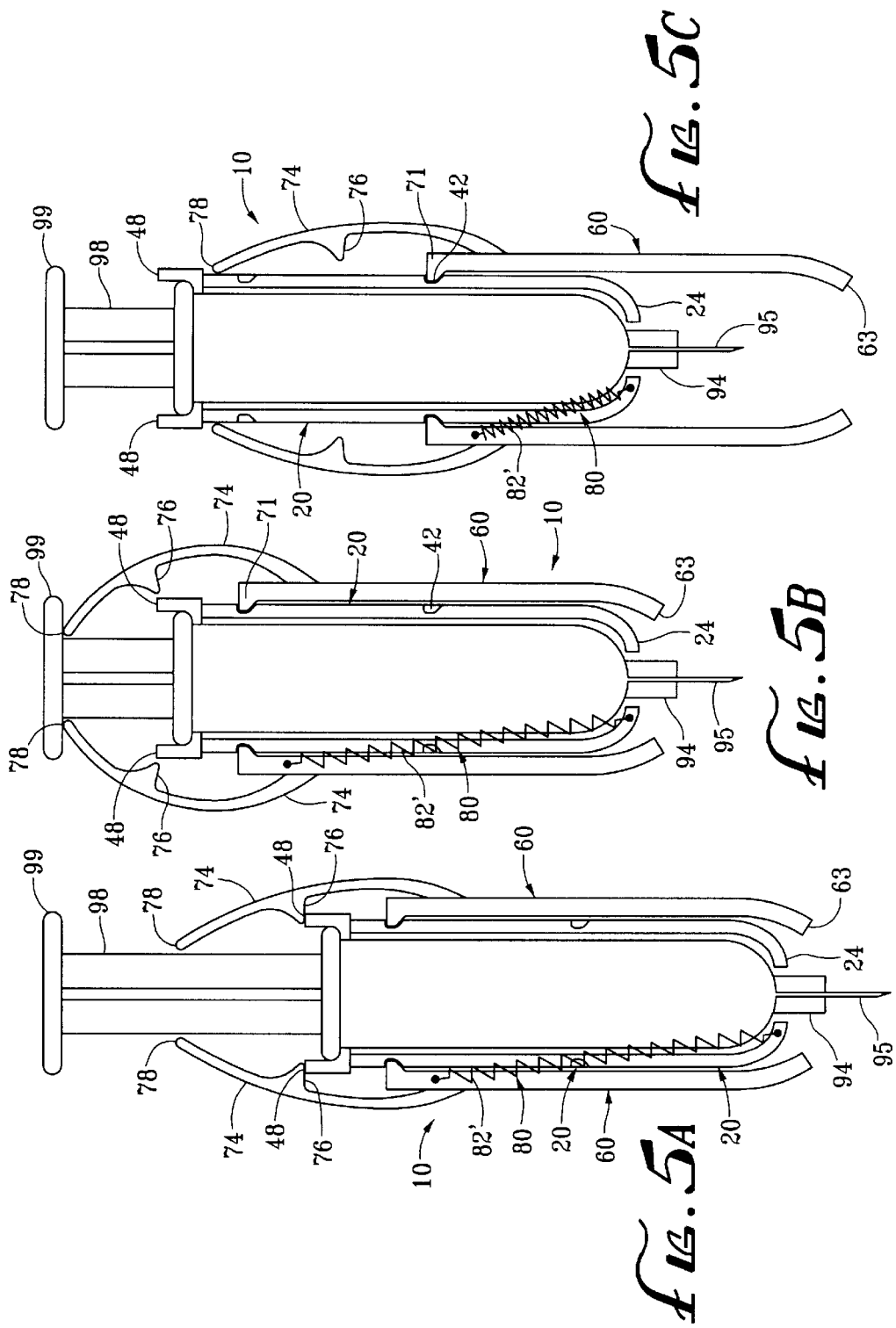

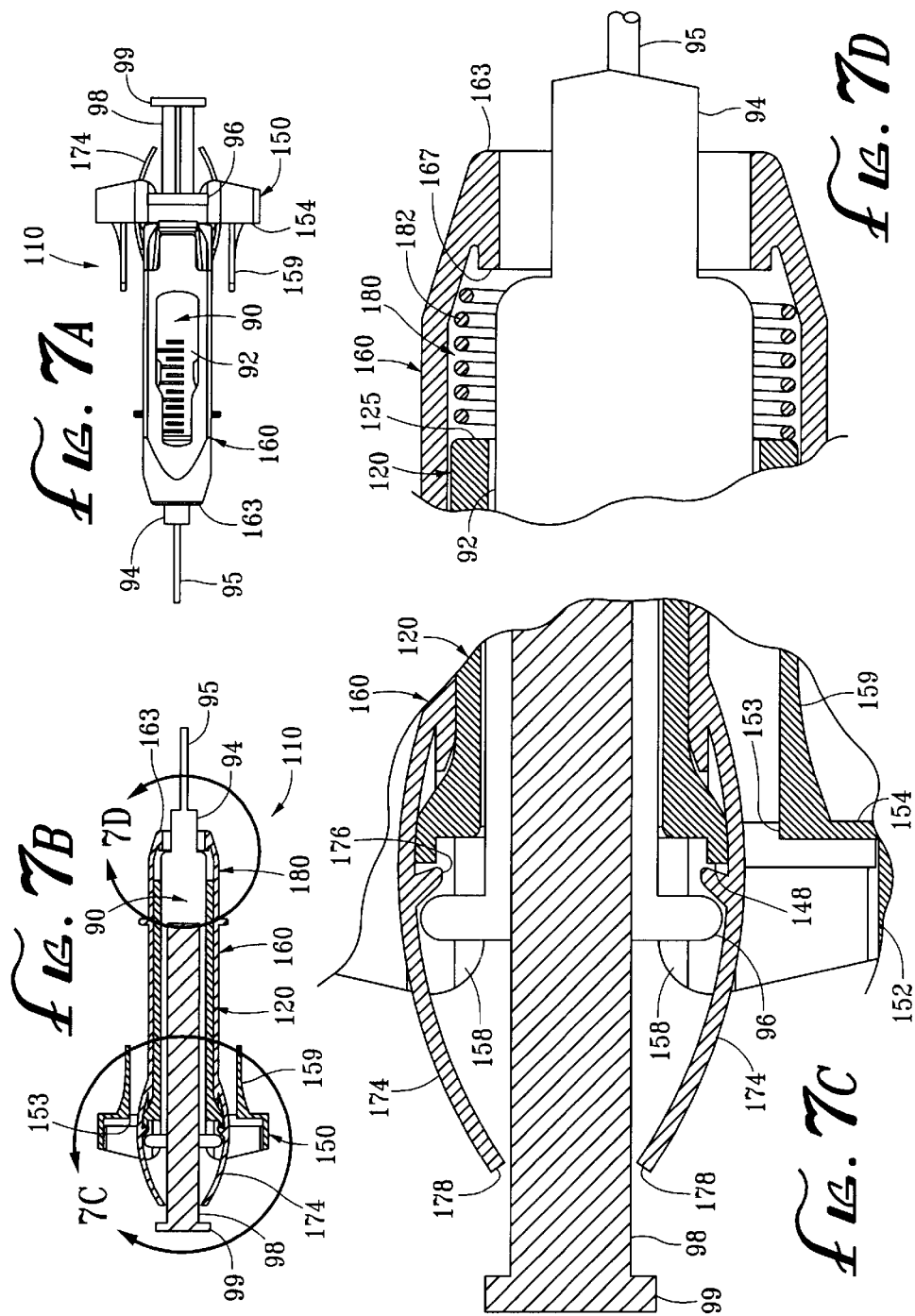

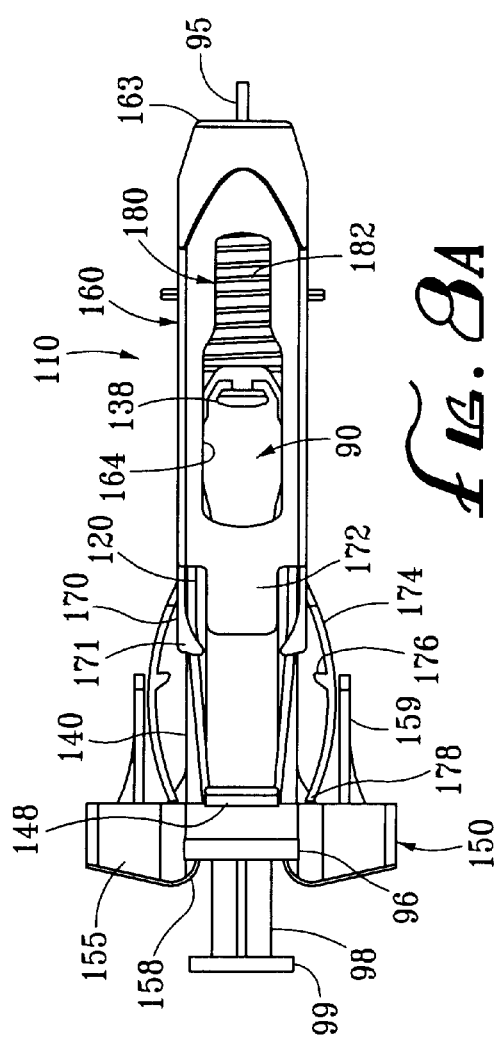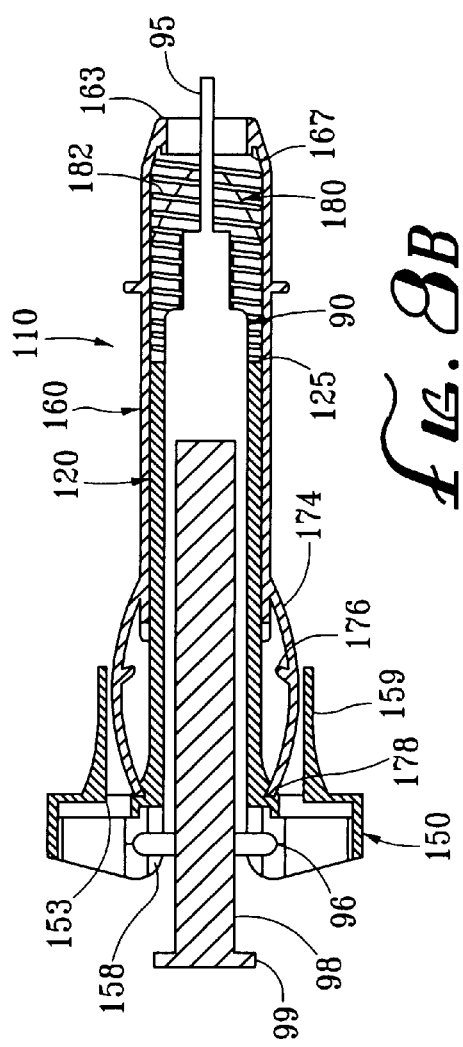

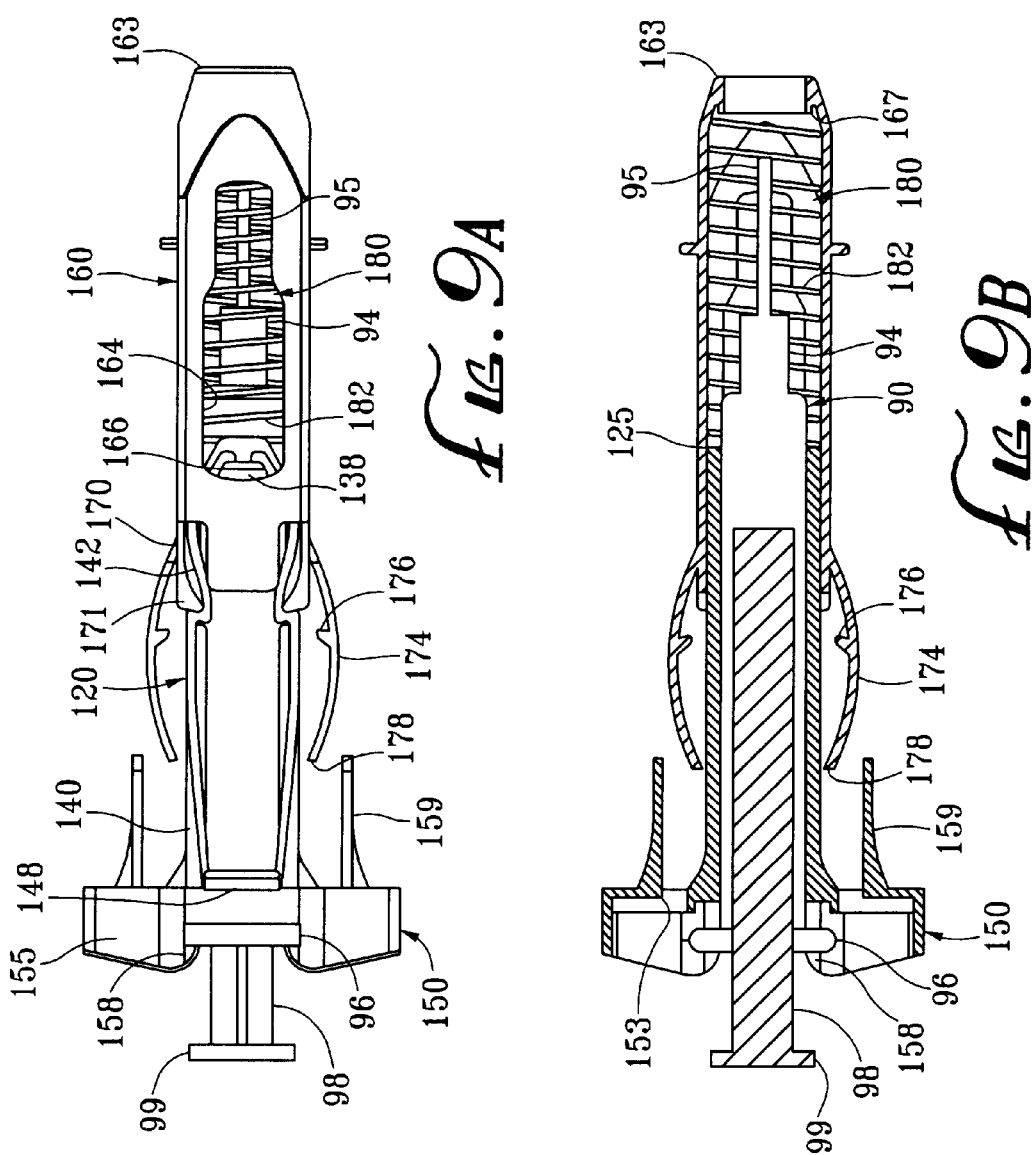

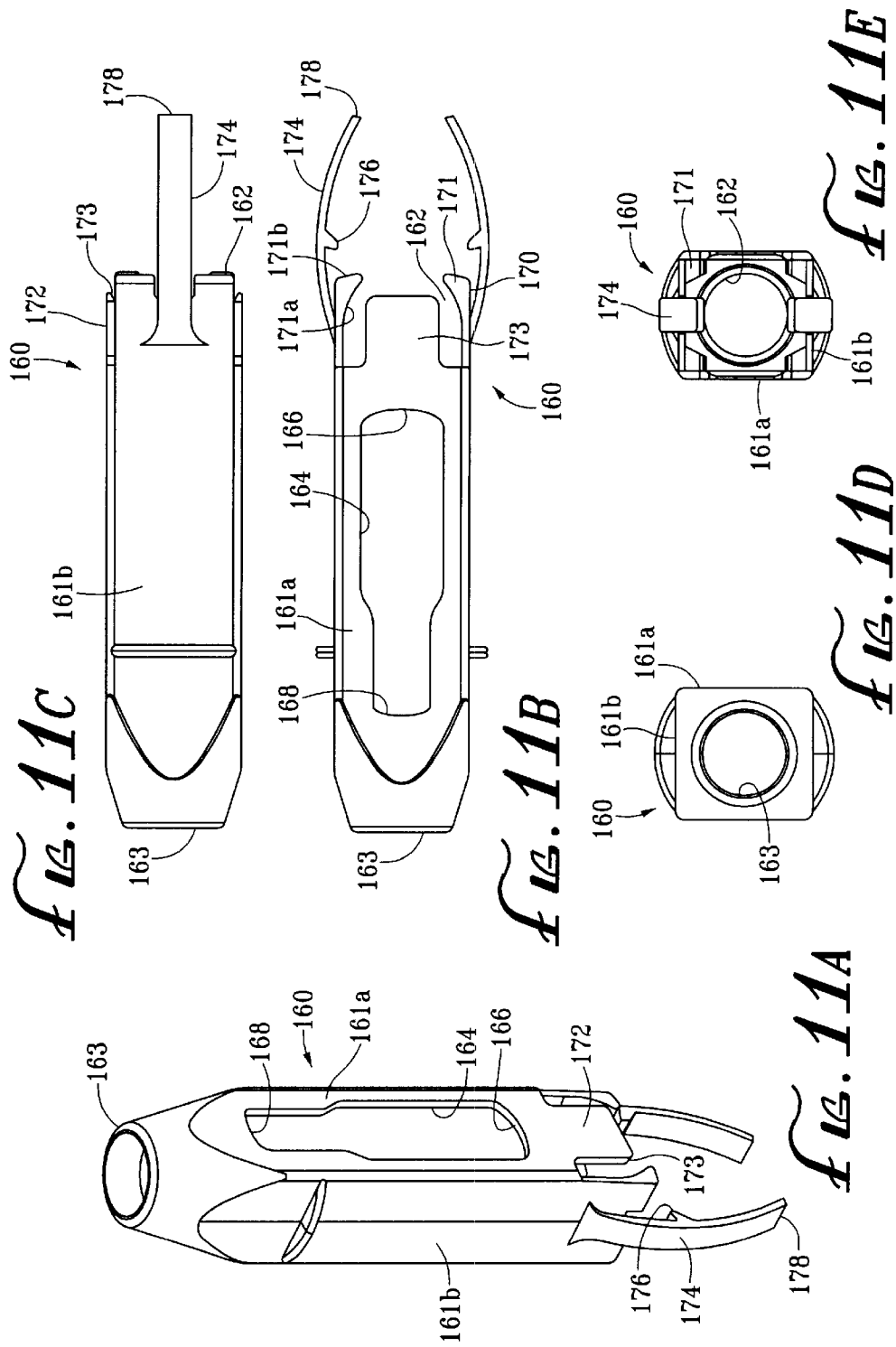

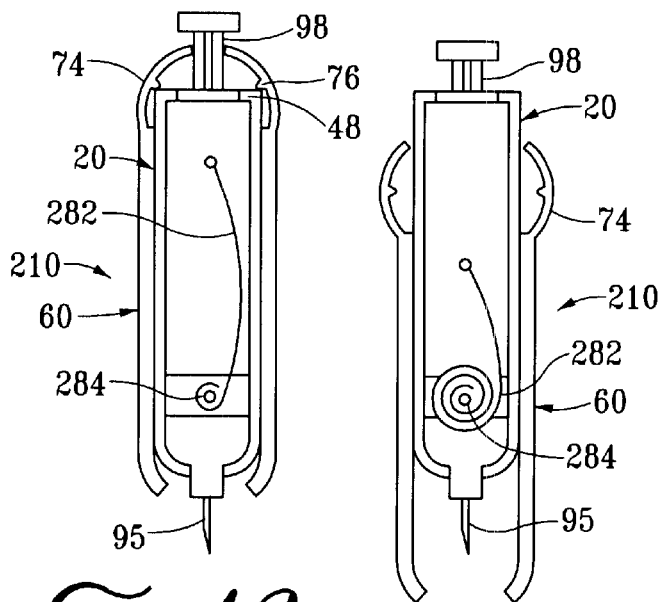
_fig.12A_  _fig.12B_
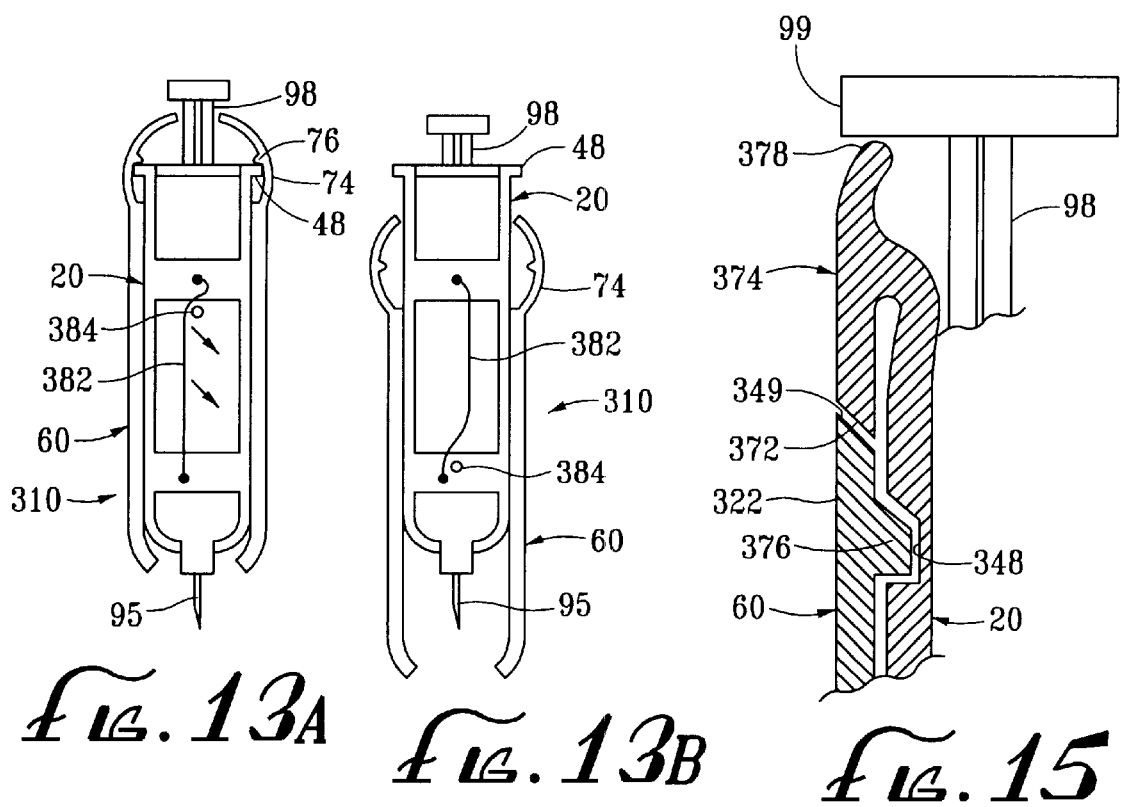
_fig.13A_  _fig.13B_  _fig.15_

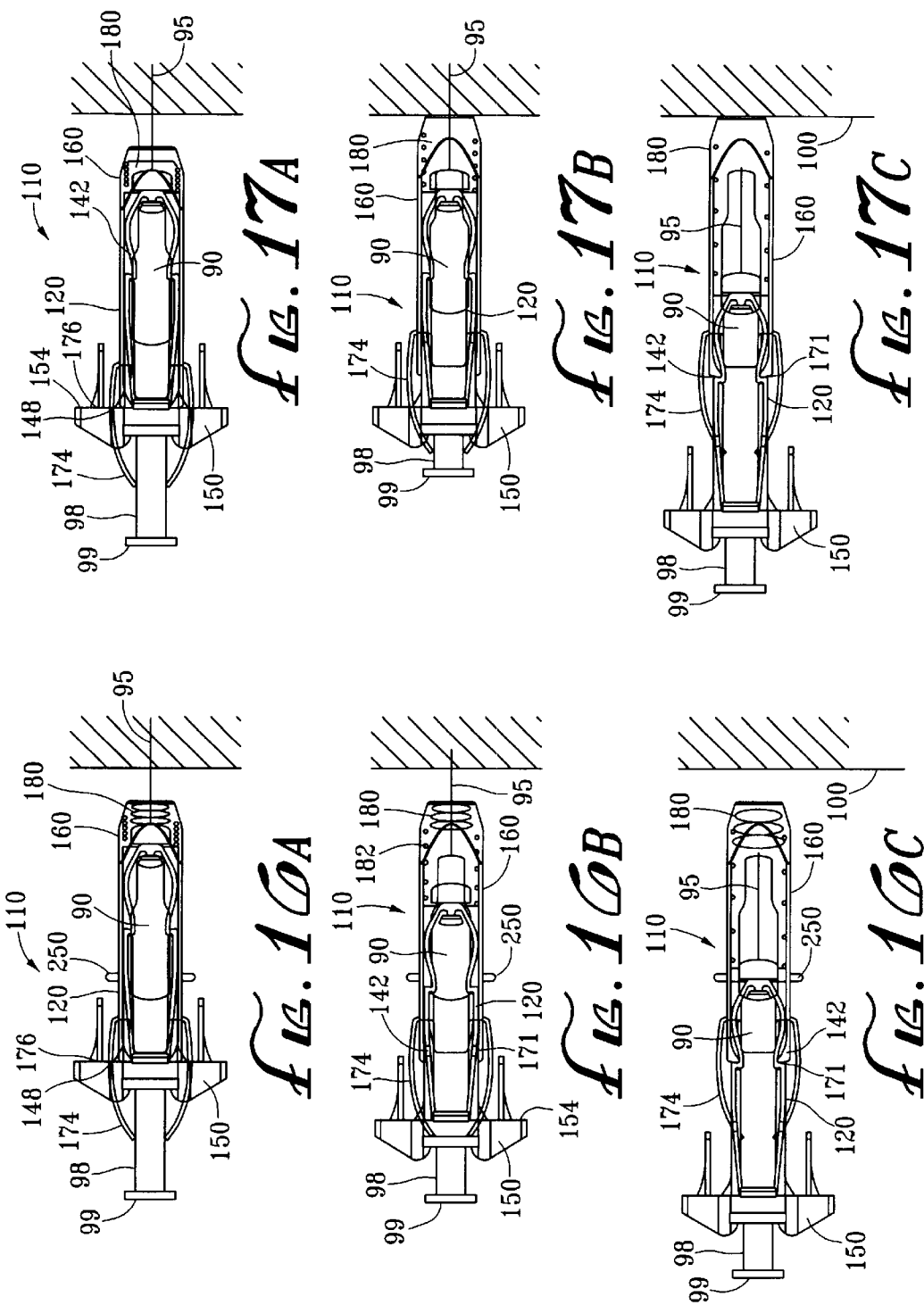

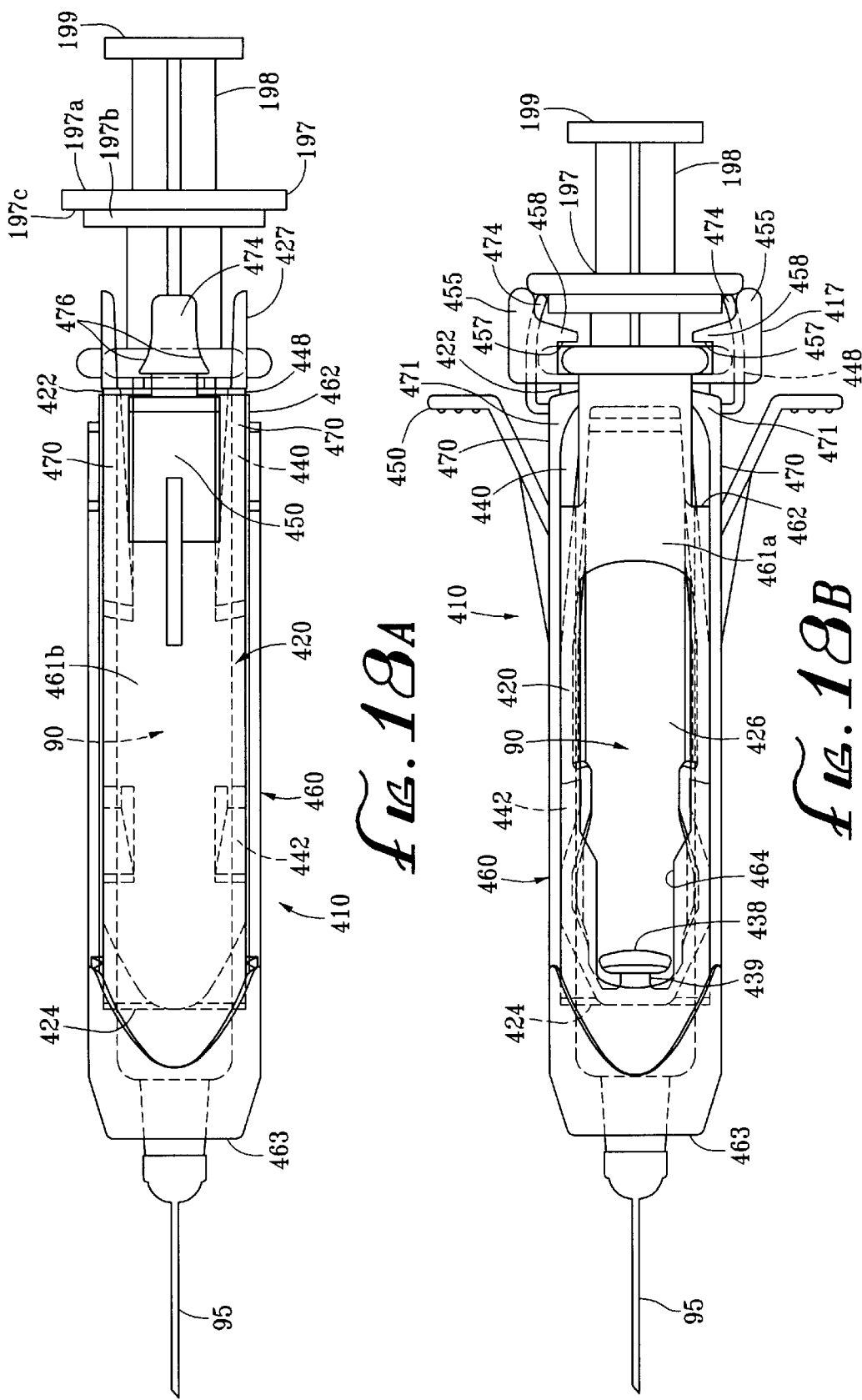

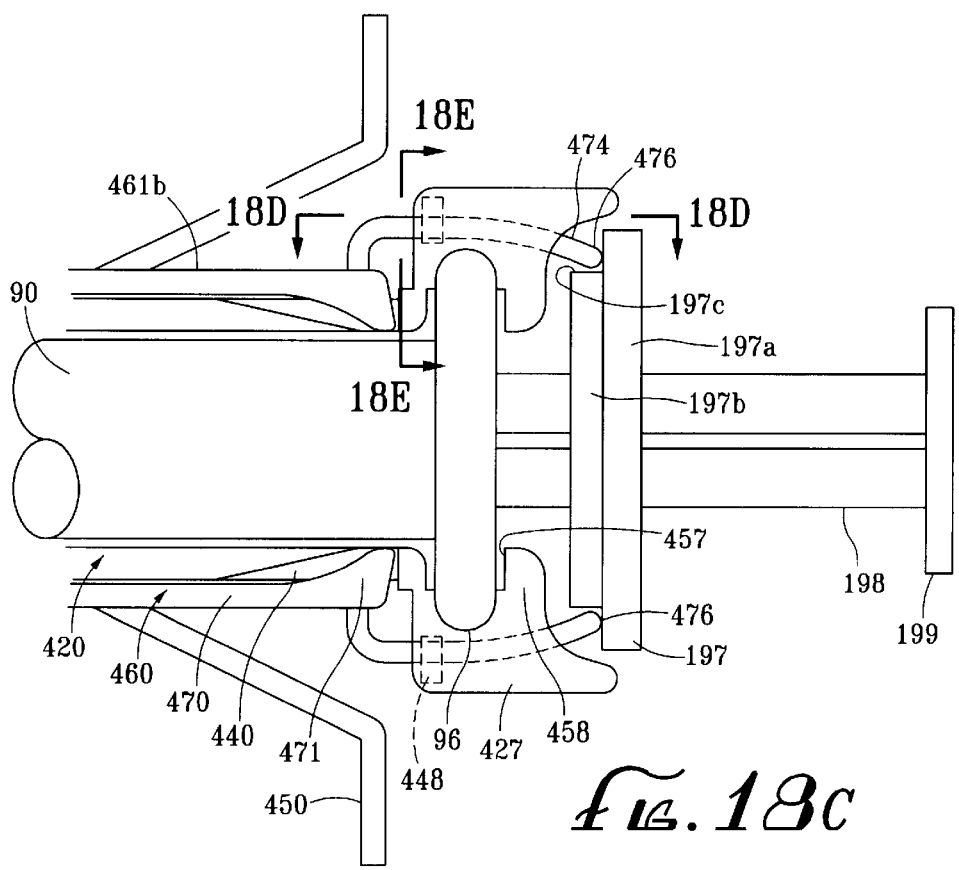

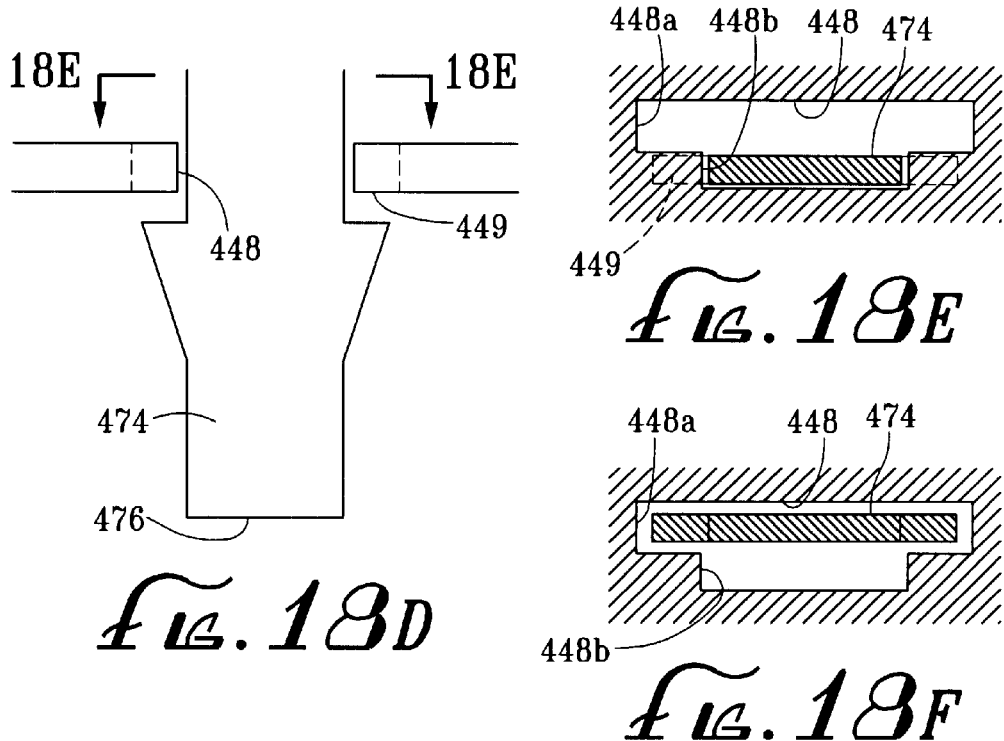
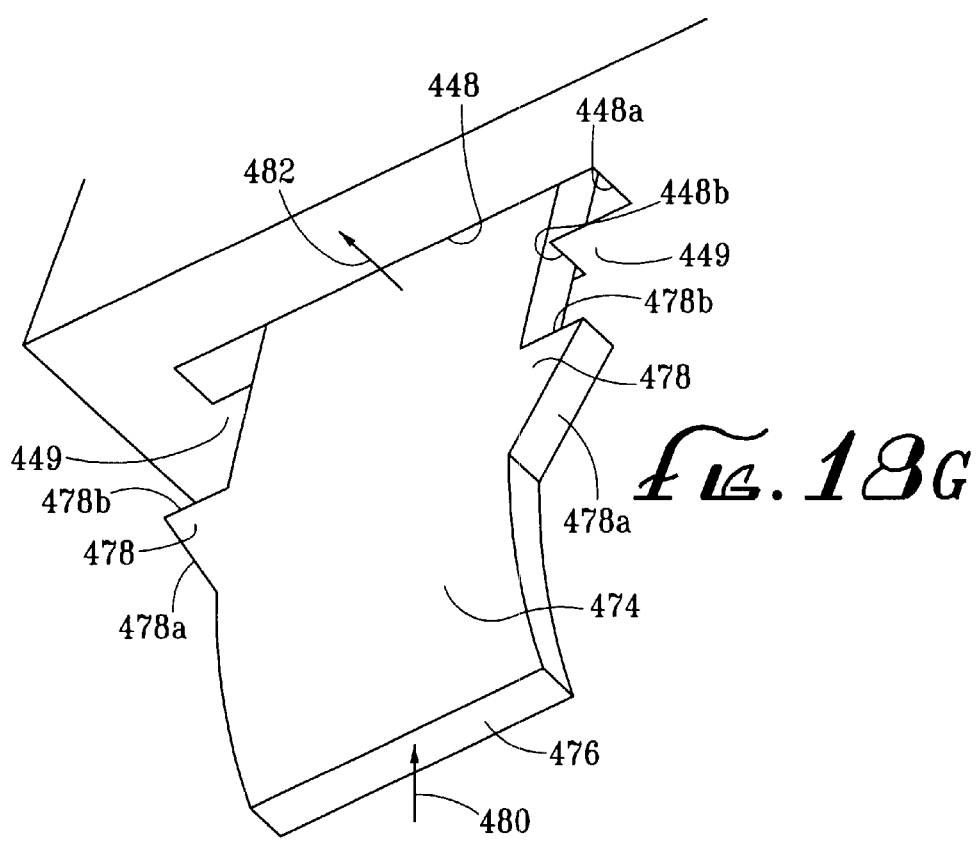

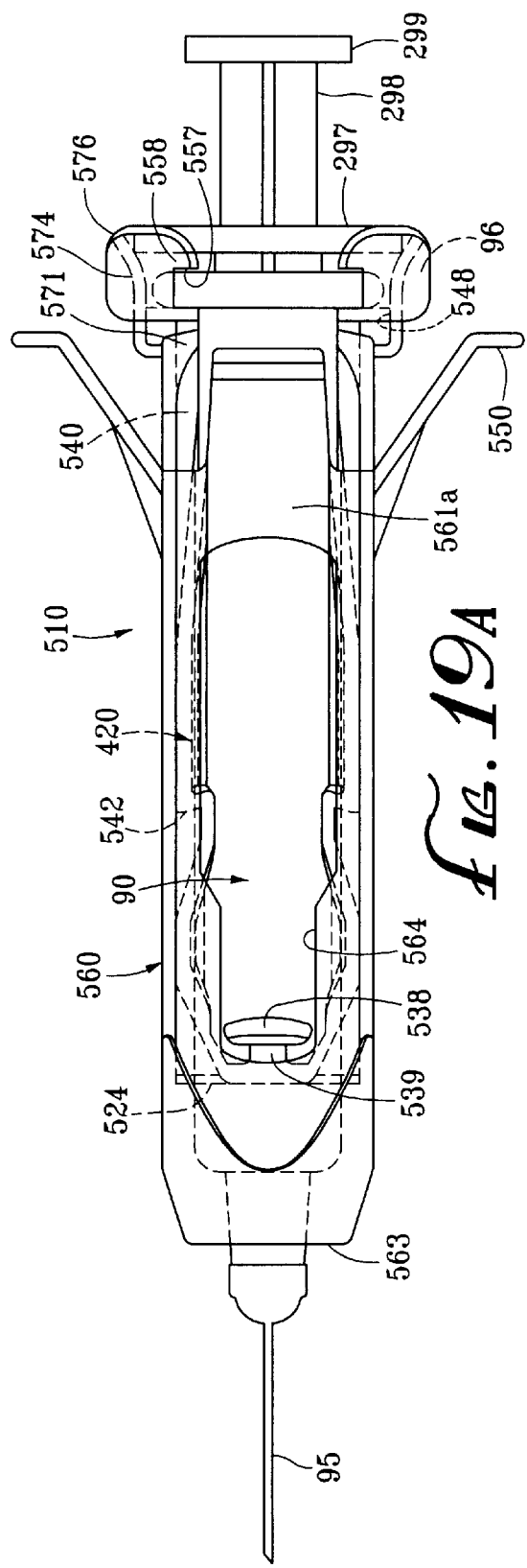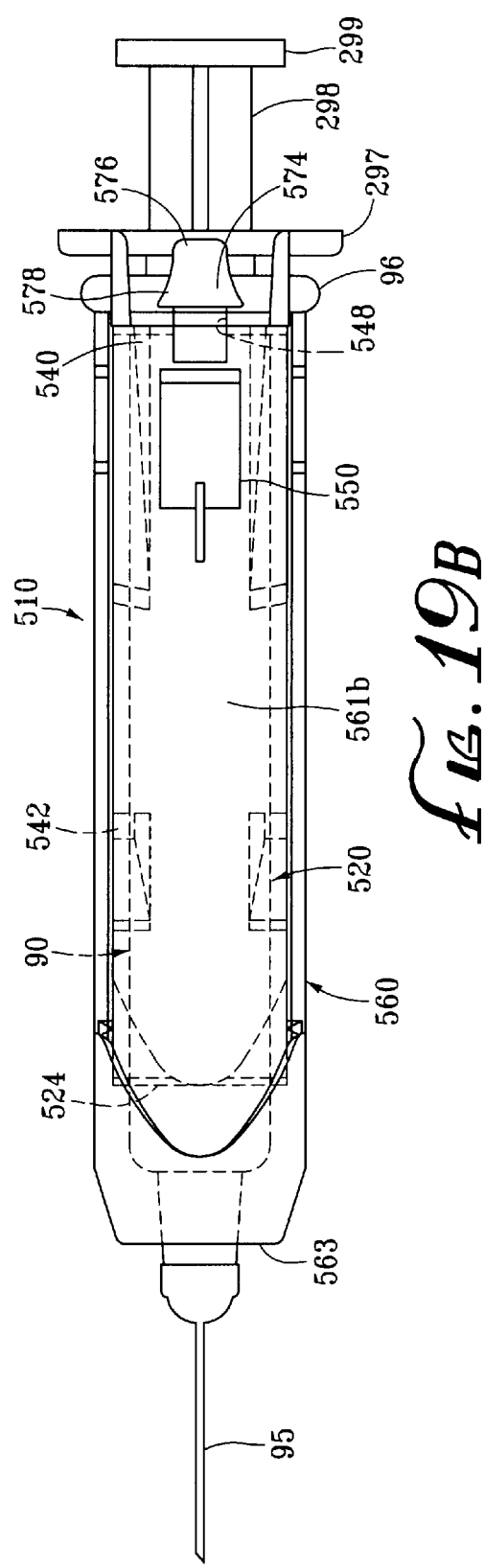

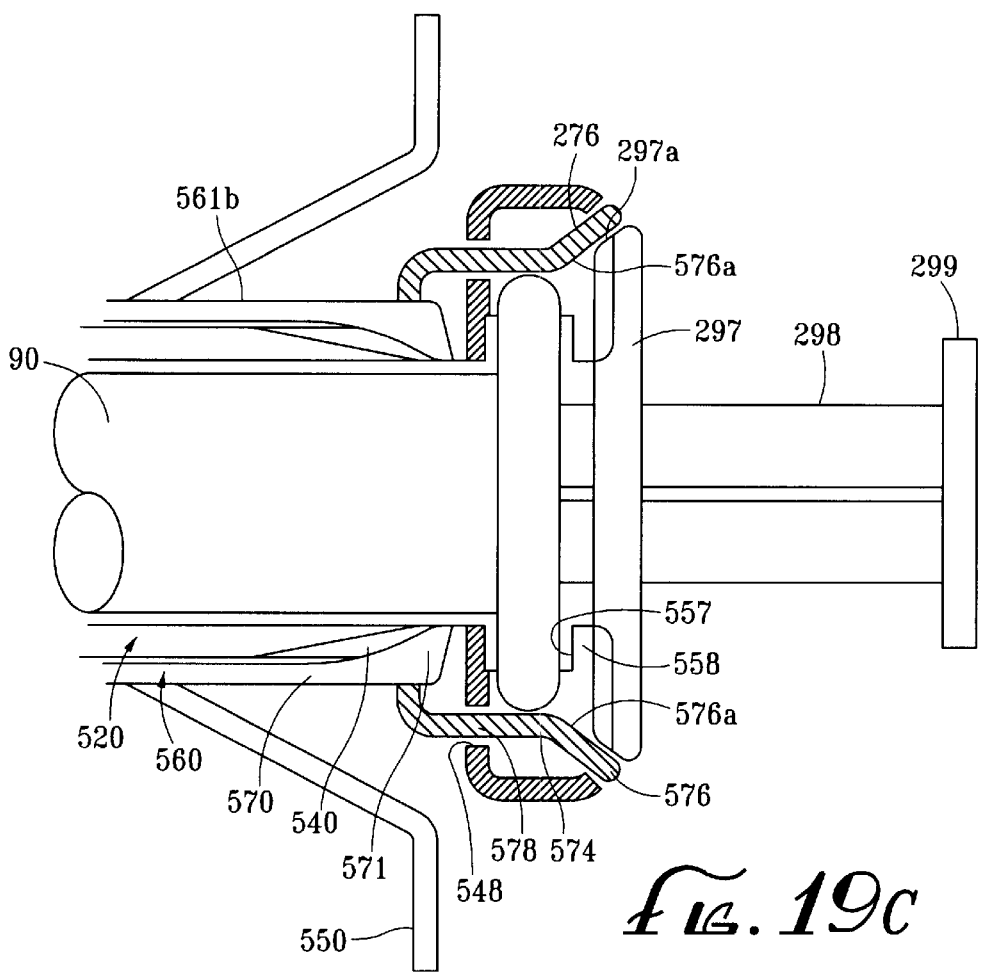

PASSIVE NEEDLE GUARD FOR SYRINGES

This is a continuation-in-part application of Ser. No. 09/566,224 filed on May 5, 2000.

FIELD OF THE INVENTION

The present invention relates generally to safety systems for syringes, and more particularly to a needle guard for a syringe that includes an automatically activated shield for covering a needle of the syringe.

BACKGROUND

Medication is often dispensed using a medicine cartridge, such as a syringe, having a barrel with a needle at one end and a plunger slidably inserted into the other end. Such cartridges are often referred to as "pre-filled syringes" because they may contain a specific dosage or volume of medication when they are initially provided, as compared to conventional syringes that are furnished empty and filled by the user before making an injection.

Alternatively, a medicine cartridge may be used, such as an ampoule or vial, that includes a penetrable seal instead of a needle on one end of the barrel, and/or a piston rather than a plunger on the other end. Such medicine cartridges are generally inserted into an adapter that includes a hollow body adapted to hold the cartridge, a plunger to engage and move the piston in the cartridge, and/or a double-ended needle to penetrate the seal and communicate with the interior of the barrel.

Because of the risk of communicable diseases, a number of syringes and adapters have been developed that are intended to prevent accidental needle sticks and/or inadvertent reuse of a syringe. Retractable needle devices have been suggested for this purpose that include a cartridge that allows a needle of the cartridge to be withdrawn into the barrel after medication is dispensed from it. For example, U.S. Pat. No. 4,973,316 issued to Dysarz discloses a syringe including a barrel having a needle assembly that is slidable within the barrel between an exposed position such that a needle on the assembly extends from the barrel and a retracted position wherein the needle assembly is withdrawn into the barrel. The needle assembly is initially locked in the exposed position, but may be disengaged upon depression of the plunger, whereupon a spring biases the assembly towards the retracted position, thereby withdrawing the needle into the barrel.

Other retractable devices have been suggested that include special plungers that may capture or otherwise engage a needle assembly upon full depression of the plunger, the needle assembly being manually or automatically withdrawn into the barrel, for example, by subsequently retracting the plunger or by a spring within the barrel. Generally, these retractable needle devices require specially designed cartridges that are substituted for a conventional syringe, and may not be used to hold commercially available pre-filled syringes or ampoules.

In addition to retractable devices, extendable needle guard devices have been suggested that include a shield that is attachable to a needle hub of a syringe or cartridge adapter. The shield may be slidable, for example, from a retracted position, coextensive with the syringe barrel such that the needle is exposed, to an extended position, covering the needle. The shield may be advanced manually between the retracted and extended positions, and may be lockable in the extended position. Alternatively, the needle guard may include a spring that automatically extends the shield to cover the needle, for example, when released by an actuator on the device. These needle guards, however, generally require specially configured needle hubs or barrels on the syringe to accommodate the attachment of the shield, and may not be used with conventional syringes or cartridges.

Alternatively, syringe holders have been suggested that include a body within which a conventional syringe or cartridge may be received, and a shield that is manually slidable with respect to the body to cover the needle. For example, U.S. Pat. No. 6,030,366, issued to Mitchell, which is assigned to the assignee of the present application, discloses a self-shielding guard that includes a body having an open proximal end for inserting a syringe into a cavity within the body, and a distal end with an opening through which a needle on the syringe may extend once received in the body. A shield is slidable over the body between retracted and extended positions to expose and cover the needle, respectively. With the shield in the retracted position and the needle exposed, an injection may be made, and then the shield may be manually advanced to the extended position. In the extended position, cooperating detents and detent pockets on the body and shield substantially permanently lock together, thereby preventing reuse of the needle, reducing the risk of accidental needle sticks, and/or facilitating disposal of the syringe.

As an alternative to requiring manual extension of a shield to cover a needle, spring-loaded devices have also been suggested. These devices often include a body and slidable shield, similar to the manual devices described above, but also may include a spring mechanism to bias the shield to advance and cover the needle. An actuator, such as a button or lever, may be activated by the user to release the shield, thereby allowing the spring mechanism to advance the shield to cover the needle. For example, U.S. Pat. No. 5,695,475 issued to Best, Jr. et al. and U.S. Pat. No. 4,923,447 issued to Morgan disclose spring-loaded syringe devices that include inner and outer sliding sleeves that include a button slidable in a longitudinal slot to selectively expose and cover a needle on the devices. A spring in the devices biases one of the sleeves to extend and cover the needle, but this bias may be manually overcome to expose the needle. Thus, these devices may not lock the extending sleeve in a covered position, and therefore may risk accidental needle exposure and/or reuse of the needle. In addition, although these devices are spring-driven, their shields may not extend unless they are manually activated, and therefore are not truly "passive," but require an affirmative decision by a user to activate their safety feature.

Accordingly, it is believed that a syringe device that automatically activates a needle shield during or following an injection would be considered useful.

SUMMARY OF THE INVENTION

The present invention is directed to needle guards for a medicine cartridge, such as a pre-filled syringe, that includes an automatically activated shield for covering a needle of the cartridge, and to methods of making and using such needle guards. In accordance with one aspect of the present invention, a passive needle guard is provided that includes a body having proximal and distal ends and a cavity therein for receiving a medicine cartridge. A shield having proximal and distal ends is attached to the body and slidable between a retracted position for exposing a needle extending from the body, and an extended position for substantially covering the needle, the shield being biased to advance towards the extended position.

Cooperating catches are provided on the body and shield for engaging one another to hold the shield in the retracted position. One or more latch members extend proximally from the proximal end of one of the shield and the body, the latch members being deflectable for disengaging the cooperating catches upon depression of a plunger coupled to the medicine cartridge, whereby the shield may automatically advance to the extended position. Preferably, the cooperating catches include a first catch on respective latch members and a second catch on the body, the latch members being resiliently deflectable radially outwardly for disengaging the first catch from the second catch. More preferably, the latch members are elongate fingers having a proximal tip that is engageable by the plunger as it is depressed to axially compress and deflect the latch members radially outwardly.

The passive needle guard also preferably includes a spring mechanism coupled to the body and the shield for biasing the shield towards the extended position. The spring mechanism may be a compression spring disposed between the body and the shield, for example, disposed concentrically within the shield adjacent to one end of the body or within elongate passages defined by the shield and/or body. Alternatively, an extension spring may be provided with respective ends attached to the shield and body. The spring mechanism may have a nonlinear spring rate such that the spring rate when the shield is in the retracted position is substantially less than the spring rate as the shield approaches the extended position.

In a preferred embodiment, the passive needle guard also includes cooperating detents on the shield and the body that are configured for engaging one another when the shield is disposed in the extended position to prevent retraction of the shield from the extended position. In addition, the passive needle guard may include a locking mechanism on the proximal end of the body, such as locking detents on a finger grip thereof, for substantially securing a medicine cartridge in the cavity.

A medicine cartridge, such as a pre-filled syringe, may be pre-assembled within the passive needle guard, or inserted by a user before making an injection. The medicine cartridge preferably includes a barrel having a needle extending from its distal end and a plunger slidably received in its proximal end. The plunger includes a radial portion for engaging the latch member when the plunger is depressed distally into the medicine cartridge. The radial portion may be provided on an intermediate region of the plunger, or may simply be a thumb pad on a proximal end of the plunger.

To assemble the passive needle guard, the proximal end of the shield may be directed over the distal end of the body. The shield may be directed towards the proximal end of the body from an extended position wherein the distal end of the shield extends beyond the distal end of the body towards a retracted position wherein the distal end of the shield is substantially coextensive with the distal end of the body. A spring may be coupled between the body and the shield, the spring biasing the shield to advance towards the extended position. The latch members on the shield may be deflected radially outwardly as the shield is directed to the retracted position to avoid contact between the catches. The latch members may then be released once the shield has attained the retracted position, the catches on the latch members engaging the catches on the body to substantially secure the shield in the retracted position.

A medicine cartridge may be inserted into the cavity in the body, preferably axially into the proximal end of the body until a locking mechanism on the body engages the medicine cartridge to substantially permanently lock the medicine cartridge therein. The latch members may need to be deflected radially outwardly as the medicine cartridge is inserted into the body, while retaining the shield in the retracted position, to accommodate a flange on the medicine cartridge. Alternatively, the cartridge may be inserted into the body before the shield is fully retracted, thereby avoiding any possible contact between the latches and a flange on the cartridge.

The passive needle guard and cartridge may then be used to perform an injection. The needle may be inserted into a patient with the shield retained in the retracted position by the cooperating catches. A plunger communicating with the medicine cartridge may be depressed to inject medication into the patient until the plunger engages the latch members extending from the passive needle guard. The plunger may then be depressed further to deflect the latch members radially to disengage the cooperating catches, and release the shield, whereupon the shield may automatically advance towards the extended position. Thus, because of the latch members and cooperating catches, the shield may be automatically activated and advanced without requiring any action from the user other than depression of the plunger, thereby providing a needle guard device that is truly passive. The needle may then be withdrawn from the patient, the released shield automatically advancing fully to the extended position to cover the needle.

When the shield is advanced to the extended position, the cooperating detents on the shield and body preferably engage one another, thereby preventing subsequent proximal movement of the shield. Thus, the shield may be substantially permanently locked in the extended position, preventing inadvertent reuse of the cartridge, minimizing the risk of accidental needle sticks, and/or facilitating safe disposal of the cartridge.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which:

FIG. 1 is a perspective view of a first preferred embodiment of a passive needle guard, in accordance with the present invention, holding a syringe.

FIGS. 2A, 2B and 2C are perspective views of a body of the passive needle guard of FIG. 1.

FIGS. 5A, 5B, and 5C are cross-sectional views of the passive needle guard of FIG. 1, showing activation of the shield as a plunger of the syringe is depressed.

FIGS. 7A and 7B are side and cross-sectional views, respectively, of a second preferred embodiment of a passive needle guard, in accordance with the present invention.

FIG. 7C is a detail of a proximal end of the passive needle guard of FIGS. 7A and 7B.

FIG. 7D is a detail of a distal end of the passive needle guard of FIGS. 7A and 7B.

FIGS. 8A and 8B are side and cross-sectional views, respectively, of the passive needle guard of FIGS. 7A and 7B, with a shield partially advanced over a needle of the guard.

FIGS. 9A and 9B are side and cross-sectional views, respectively, of the passive needle guard of FIGS. 7A and 7B, with the shield fully advanced over the needle.

FIG. 11A is a perspective view of a shield for the passive needle guard of FIGS. 7A and 7B.

FIGS. 11B–11E are side, top, and end views of the shield of FIG. 11A.

FIGS. 12A and 12B are cross-sectional side views of a passive needle guard, including a coil spring mechanism, with its shield in retracted and extended positions, respectively.

FIGS. 13A and 13B are cross-sectional side views of a passive needle guard, including a leaf spring mechanism, with its shield in retracted and extended positions, respectively.

FIG. 15 is a cross-sectional view of a passive needle guard, including latch member that has a ramped distal edge, cooperating catches, and a thumb pad, in accordance with yet another embodiment of the present invention.

FIGS. 16A–16C are side views of a passive needle guard, showing a method of injecting medication using a syringe received in the guard, in accordance with the present invention.

FIGS. 17A–17C are side views of a passive needle guard, showing another method of injecting medication using a syringe received in the guard, in accordance with the present invention.

FIGS. 18A and 18B are side views of another preferred embodiment of a passive needle guard, in accordance with the present invention.

FIG. 18C is a detail of a proximal portion the guard of FIGS. 18A and 18B.

FIG. 18D is a cross-sectional side view of the latch member and mating catch, taken along line D—D of FIG. 18C.

FIGS. 18E and 18F are details of the latch member and mating catch, taken along line E—E of FIGS. 18C and 18D.

FIG. 18G is a perspective view of the latch member and mating catch of FIG. 18C.

FIGS. 19A–19B are side views of yet another preferred embodiment of a passive needle guard, in accordance with the present invention.

FIG. 19C is a cross-sectional detail of a proximal portion of the guard of FIGS. 19A and 19B.

DETAILED DESCRIPTION OF THE PREFERRED EMBODIMENTS

Figure 2C:
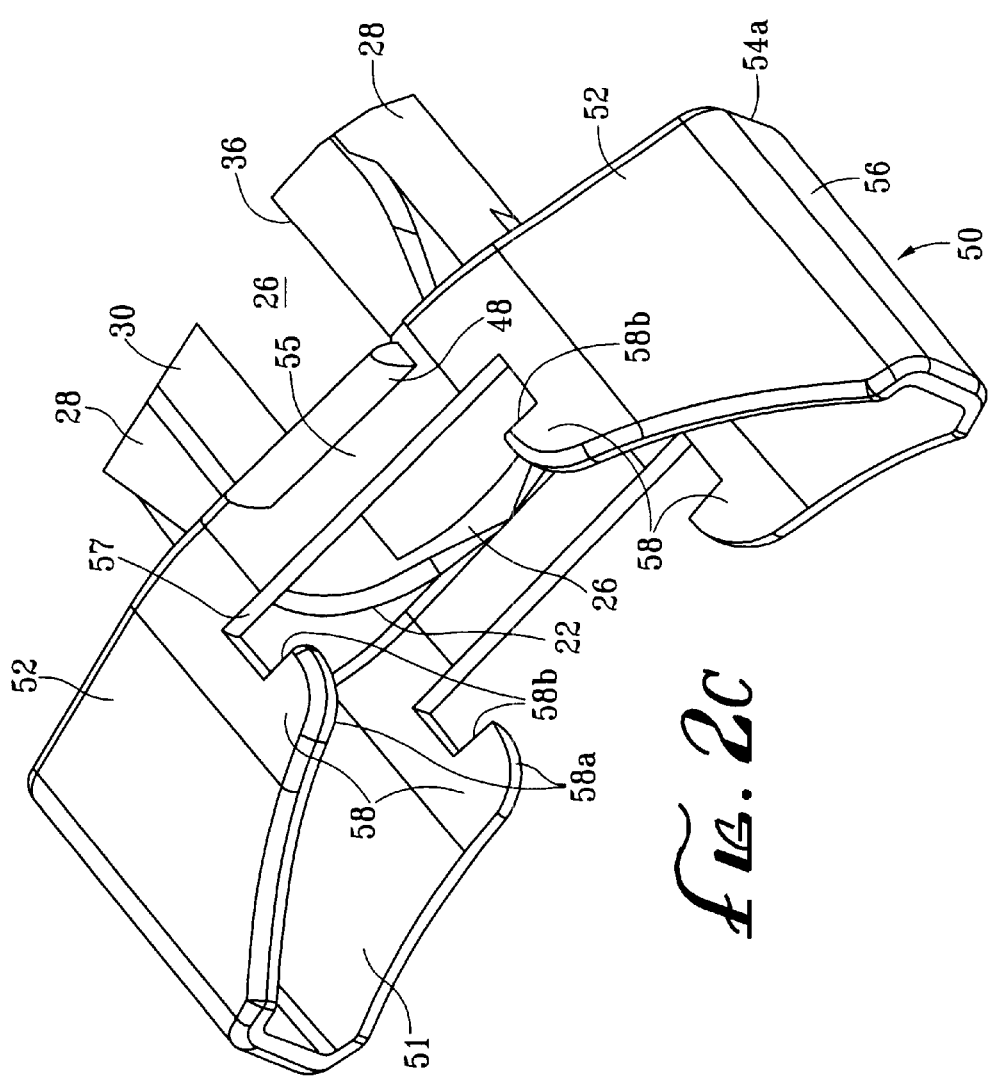

Turning now to the drawings, FIGS. 1–6 show a first preferred embodiment of a passive needle guard 10 for holding a syringe 90, in accordance with the present invention. Generally, the passive needle guard 10 includes three parts, namely a body 20 for receiving and holding the syringe 90, a shield 60 slidably attached to the body 20, and a spring mechanism 80. Both the body 20 and the shield 60 are generally molded from plastic, such as polypropylene, k-resin, or polycarbonate, and are preferably substantially clear and colorless to facilitate observation of the syringe 90 received therein. Alternatively they may be translucent or opaque, and may be colored, such as a latex color or a flesh tone.

Turning to FIGS. 2A–2C, the body 20 has opposing side rails 28 defining two elongate openings or windows 36 extending at least partially between a proximal end 22 and a distal end 24 of the body 20. The two side rails 28 generally have a "C" shape defining a cavity 26 extending axially from the proximal end 22 to the distal end 24 of the body 20. Alternatively, instead of the side rails 28, the body 20 may include a substantially rectangular body having four side walls (not shown). If a four-walled body is provided, it may be desirable to provide one or more elongate openings or windows in one or more of the side walls, preferably in two walls on opposite sides of the body 20.

The inside surfaces 30 of the rails 28 are preferably concave, conforming substantially to the outer diameter of a conventional pre-filled syringe. Alternatively, guide rails, resilient ribs, and the like (not shown) may be provided on the inside surface 30 to facilitate insertion of a cartridge into the cavity 26 and/or to provide lateral support for a syringe received therein. Co-pending application Ser. No. 08/942, 938, filed Oct. 2, 1997, the disclosure of which is expressly incorporated herein by reference, discloses exemplary resilient rib structures that may be provided within the body 20. The outer surfaces of the side rails 28 define a substantially rectangular cross-section for the body 20, providing a substantially rigid structure for protecting the syringe 90 received within the body 20.

As best seen in FIG. 2B, a substantially rigid collar 32 is molded on the distal end 24 of the body, the collar 32 preferably having a substantially annular shape. The collar 32 defines an opening 34 for allowing a needle and needle cover on a syringe (not shown) received in the cavity 26 to extend distally beyond the body 20. The opening 34 preferably has a diameter smaller than the cavity 26, such that the distal end 24 substantially retains the syringe inside the cavity 26 preventing distal movement. Alternatively, the distal end 24 may be tapered or otherwise partially obstructed for engaging the distal end of the syringe and/or preventing distal movement of the syringe. Stop tabs 38 may be molded directly on the distal end 24 of the body 20, preferably on two opposite sides of the distal end 24, or alternatively, may be provided on a cantilever member (not shown), such as that disclosed in U.S. Pat. No. 6,030,366, issued to Mitchell, the disclosure of which is expressly incorporated herein by reference.

As best seen in FIG. 2C, a finger grip 50 is molded on the proximal end 22 of the body 20 that includes a pair of wing-like members or flanges 52 generally defining a "T" shape. Each wing-like member 52 includes a distal surface or finger ledge 54, and an outer gripping surface 56 extending proximally from the outer edge 54a of the finger ledge 54. The outer gripping surface 56 may include a lip, grooves, or other irregularities (not shown) protruding radially from its proximal end or set in the surface 56, for example, to facilitate a user holding the finger grip 50. Lateral surfaces 55 extend proximally from the finger ledges 54 between the gripping surfaces 56, thereby defining a recess 51 communicating with the cavity 26 in the body 20. Alternatively, the recess 51 may be eliminated and/or the finger grip 50 may be shortened, for example, to simply be a flat transverse flange for accommodating shorter cartridges (not shown).

A catch or tab 48 may be molded or otherwise extend from one of and preferably both of the lateral surfaces 55 of the finger grip 50. Alternatively, the catch 48 may be provided on the proximal end 22 of the body 20 adjacent the finger grip 50 (not shown).

In a preferred embodiment, a locking mechanism is provided on the finger grip 50 and/or on the proximal end of the body 20 for engaging a flange of a syringe (not shown) received in the cavity 26, and thereby substantially securing the syringe within the body 20. Preferably, the locking mechanism includes a plurality of locking detents 58 at least partially defining an aperture or slot 57 that are formed in lateral surfaces 55 of the finger grip 50 for receiving the flange therein. Alternatively, other locking mechanisms may be provided on the proximal end 22 of the body 20, such as those disclosed in the co-pending application referenced above. In a further alternative, other known mechanisms may be used to secure a syringe within the body 20, such as locking detents or a collet mechanism (not shown) on the distal end 24 of the body 20.

Returning to FIG. 2A, one or more sets of detent pockets may be molded into the body 20 to facilitate securing the relative movement of the shield 60 and body 20. In a preferred embodiment, a set of proximal detent pockets 40 is provided adjacent the finger grip 50, and a set of distal detent pockets 42 is provided at a more distal location on the body 20. Preferably, the proximal detent pockets 40 have sloping distal edges 40a and substantially blunt proximal edges 40b. The distal detent pockets 42 also have substantially blunt, and preferably oblique, proximal edges 42b.

Figure 3:
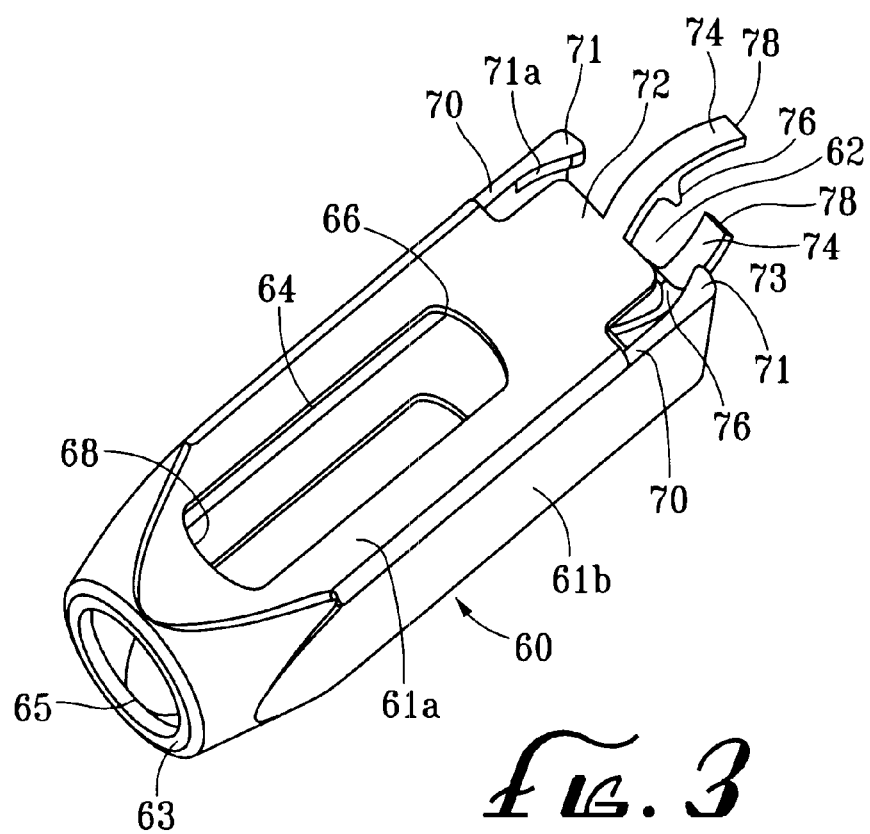
FIG. 3 is a perspective view of a shield of the passive needle guard of FIG. 1.

Turning to FIG. 3, the shield 60 is a tubular member adapted to slidably fit on the body 20, preferably having a substantially rectangular interior shape that conforms to the shape of the body 20. The shield 60 includes four side walls 61a, 61b, an open proximal end 62, and an open distal end 63. Assembly tabs 72 with sloping or ramped interior surfaces 73 are molded into and extend proximally from the side walls 61a.

One or more latch members or fingers 74 extend proximally from the shield 60, preferably molded to each of the assembly tabs 72. Alternatively, the latch members 74 may be made as separate pieces that are bonded or otherwise attached to the shield 60, for example, to the outside of the assembly tabs 72, using an adhesive and the like. Each latch member 74 includes an inwardly disposed catch or tab 76 located on an intermediate portion of the latch member 74 between the assembly tab 72 and a tip 78 of the latch member 74. The latch members 74 are preferably provided from a substantially flexible material such that they are resiliently deflectable for deflecting the intermediate portion radially outward, and thereby disengaging the catch 76 from the mating catch 48 on the body 20, but are biased to return inwards to promote engagement with the mating catches 48 on the body 20, as described further below.

A plurality of detent arms 70, preferably in opposing pairs, and a plurality of detents 71 are integrally molded directly onto or otherwise attached to the side walls 61b. The detents 71 preferably have shapes corresponding substantially to the shapes of the detent pockets 40, 42 in the body 20. Distal edges 71a of the detents 71 are preferably ramped to facilitate slidable engagement with the distal surfaces 40a of the proximal detent pockets 40. Proximal edges 71b of the detents 71 are substantially blunt, and preferably oblique, for positively engaging the proximal edges 42b of the distal detent pockets 42 and locking the shield 60 in an extended position, as described further below. Additional information on detents and detent pockets for use with the present invention are described in the Mitchell patent referenced above. In addition, the detent arms 70 may include indents (not shown) for controlling the flexural strength of the detent arms 70, as the arms 70 may vary in size and thickness in embodiments adapted to accommodate a variety of syringes.

At least one wall 61a, and preferably the two opposite walls 61a, include an elongate opening or window 64 therethrough. The windows 64 may facilitate observation of the syringe received in the body 20, and also provide a traveling slot for the stop tabs 38 on the body 20. The windows 64 have a proximal edge 66 and a distal edge 68 defined by the wall 61a that limit the relative movement of the shield 60 to the body 20, as explained below. Alternatively, the windows 64 may be divided by a cross-member (not shown) molded into the wall 61a that extends transversely across the window 64 if it is desired to further limit movement of the shield 60.

Optionally, the side walls 61a, 61b may include wings, a ring, or similar finger holds (not shown) extending radially from the shield 60 to ease movement of the shield 60 in relation to the body 20. In addition, the side walls 61a, 61b may provide a flat surface onto which a label may be applied, for example to identify the drug, medication, or other fluid contained within the pre-filled syringe 90 received within the guard 10, or an embossed pattern may be molded, possibly including a name or a logo.

Figure 4A:
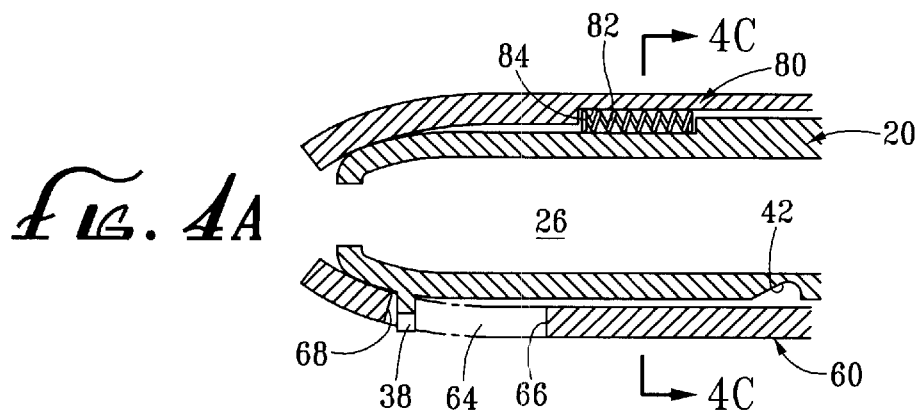
FIGS. 4A, 4B, and 4C are cross-sectional views of the passive needle guard of FIG. 1, showing a spring mechanism for advancing the shield with respect to the body between retracted and extended positions.
Figure 4B:
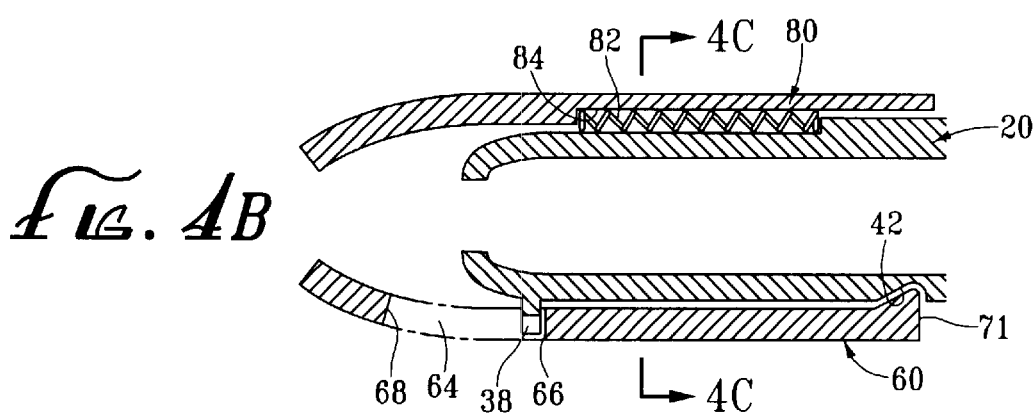
Figure 4C:
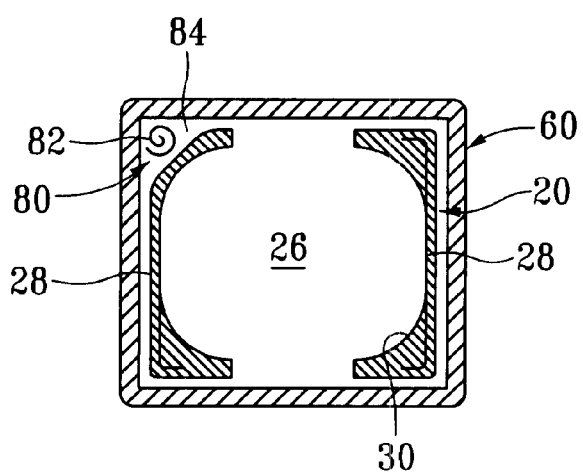
Figure 10A:
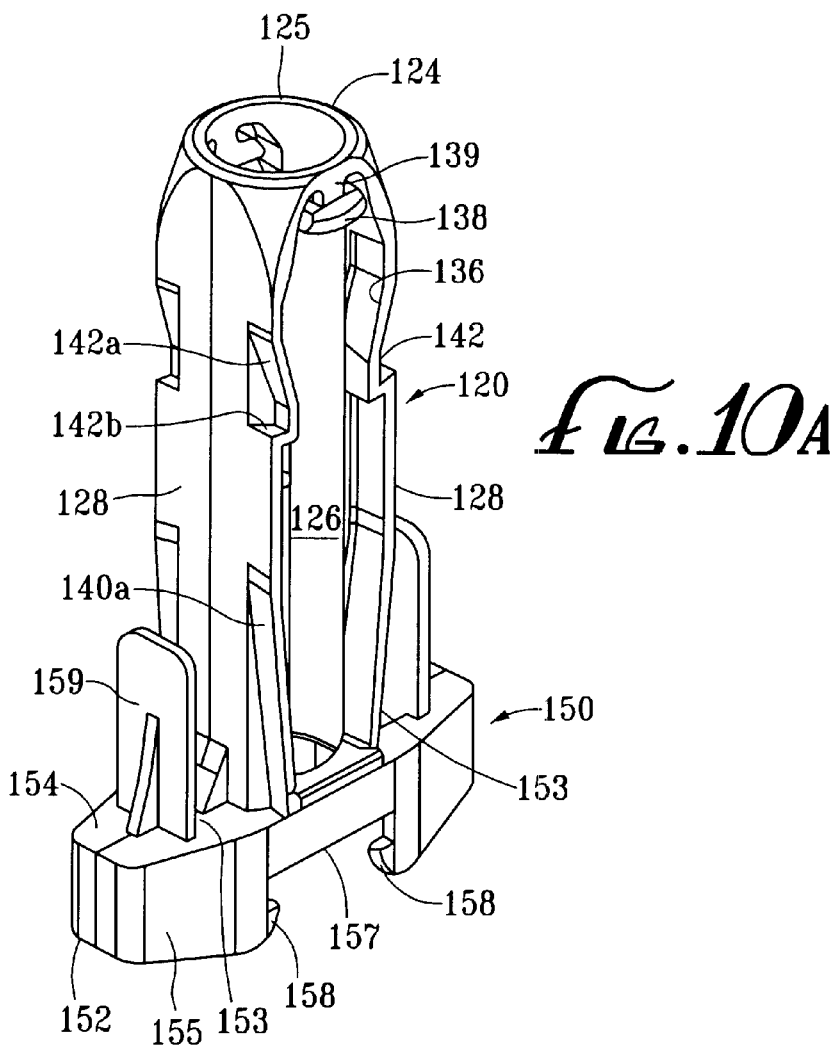
FIG. 10A is a perspective view of a body for the passive needle guard of FIGS. 7A and 7B.
Figure 10B:
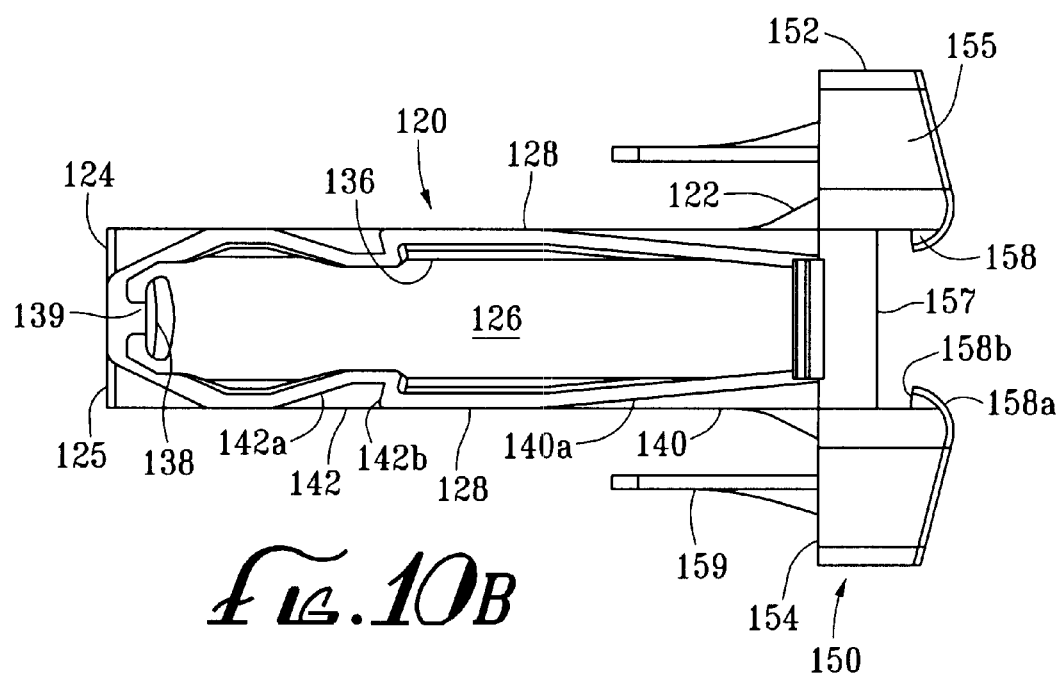
FIGS. 10B–10E are side, top, and end views of the body of FIG. 10A.
Figure 10C:
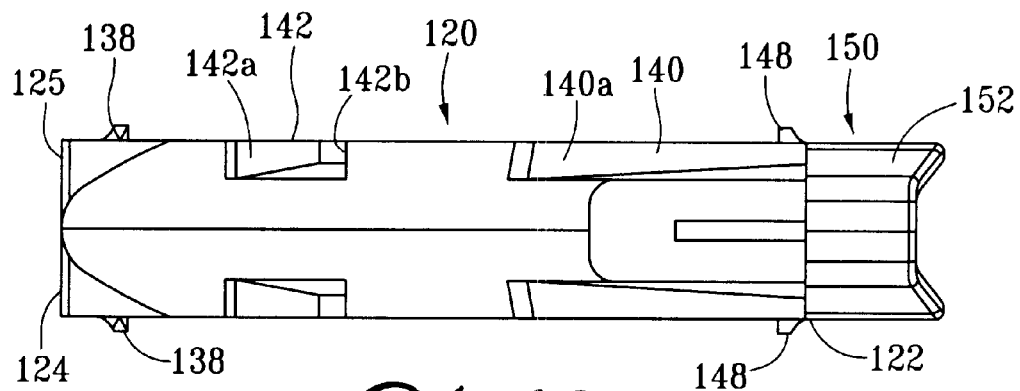
Figures 10D, 10E:
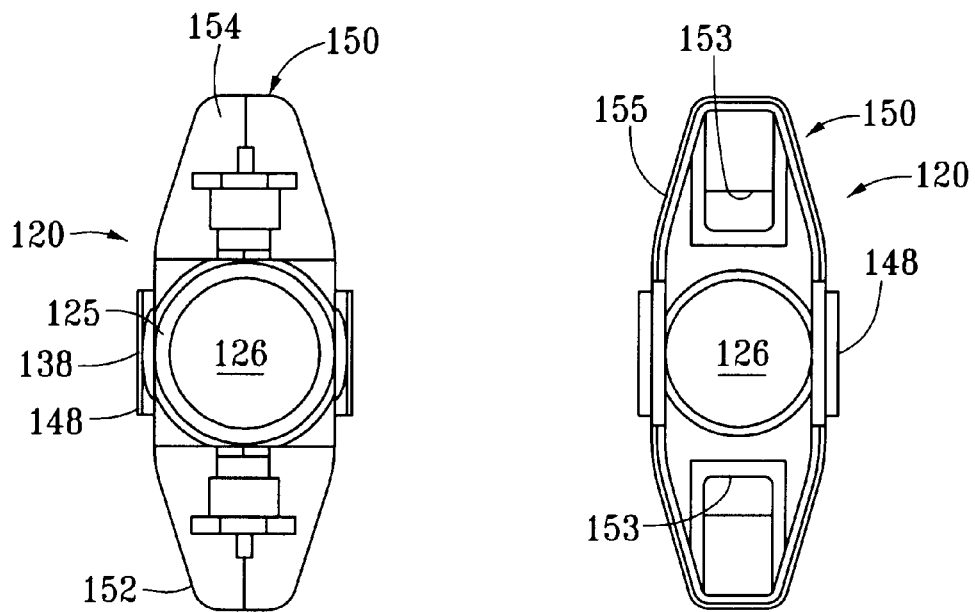

Turning to FIGS. 4A–4C, the spring mechanism 80 preferably includes a spring 82 that is coupled to the body 20 and the shield 60 to bias the shield 60 towards an extended position (FIG. 4B). For example, the body 20 and shield 60 may together define an elongate passage 84 within which a helical compression spring 82 may be compressed when the shield 60 is in a retracted position (FIG. 4A). The passage 84 is preferably provided in a corner of the body 20, as best seen in FIG. 4C. Alternatively, a plurality of springs and passages (not shown) may be provided, for example, a pair of springs and passages in diagonally opposite corners of the body 20 to minimize the risk of subjecting the shield 60 to torque as it advances from the retracted to the extended position as may occur if only a single off-center spring is used.

In further alternatives, one or more helical extension springs 82' may be provided that have respective ends that are secured to the body 20 and shield 60, as is shown schematically in FIGS. 5A–5C. The extension spring 82' may be provided in a passage or cavity within the shield and/or between the shield and body (not shown). The spring may be under tension when the shield 60 is disposed in the retracted position, thereby biasing the shield 60 towards the extended position.

Alternative spring structures may also be provided that may be coupled to the body 20 and shield 60. For example, FIGS. 12A and 12B show a passive needle guard 210 including a coil spring 282 that has one end mounted around a hub 284 on a body 20 and/or within a housing (not shown) and the other end secured to a shield 60. The coil spring 282 may be unwound as the shield 60 is retracted to the retracted position (FIG. 12A), but be biased to wind back around the hub 284 to advance the shield 60 towards the extended position (FIG. 12B). In a further alternative, as shown in FIGS. 13A and 13B, a passive needle guard 310 may include a leaf spring 382 with ends fixed to a body 20, for distally biasing a hub 384 coupled to a shield 60. The shield 60 may be retracted, thereby deflecting the leaf spring 382 (FIG. 13A), but when the shield 60 is released, the hub 384 and consequently the shield 60 may be advanced to the extended position as the leaf spring 382 returns to its relaxed, undeflected state (FIG. 13B).

In addition, if desired, the spring mechanism may have a nonlinear spring rate, preferably having a spring rate when the shield 60 is disposed in the retracted position that is substantially less than its spring rate when the shield 60 approaches the extended position. A nonlinear spring rate may be useful to provide a passive needle guard that is "softer" upon activation, i.e., the spring 82 may apply a substantially lower force to the shield 60 when it is initially released from the retracted position than when it approaches the final extended position. For example, the thickness of the spring material may be varied along its length, different materials may be used for different portions of the spring, and the like. This "softer" spring may minimize the force with which the shield 60 contacts a patient being injected using the passive needle guard 10, and thereby reduce the discomfort or anxiety that may be experienced by the patient. For example, as explained below, the shield 60 may be activated with a softer force, such that the shield 60 more gently contacts the patient, but when the needle is withdrawn from the patient, a stronger force may be applied to the shield 60 to ensure that it advances completely to the extended position.

Returning to FIG. 1, the passive needle guard 10 is generally provided with the body 20 and shield 60 pre-assembled with the shield 60 in the retracted position. In the retracted position, the catches 76 on the latch members 74 substantially engage the mating catches 48 on the body, thereby securing the shield 60 in the retracted position against the bias provided by the spring mechanism 80. In addition, the detents 71 may be received in the proximal detent pockets 40, thereby providing additional security to hold the shield 60 in the retracted position. Alternatively, the proximal detent pockets 40 may be used merely to receive the detents 71 and thereby allow the detent arms 70 to return to a relaxed state, rather than extending outward along the outer surface of the body 20. In a further alternative, the proximal detent pockets 40 may not be needed and may be eliminated.

With reference to FIGS. 1–6, to assemble the passive needle guard 10, the distal end 24 of the body 20 (see FIG. 2A) is inserted into the open proximal end 62 (see FIG. 3) of the shield 60, with the window 36 in the body 20 aligned with the side wall 61a of the shield 60 having the window 64 therein. The spring 82 may be positioned within the passage 84 and/or secured to the body 20 and shield 60 in a conventional manner. As the body 20 is inserted, the stop tab 38 engages a tapered interior edge (not shown) of the assembly tab 72 on the shield 60, allowing the stop tab 38 to pass under the side wall 61a. After the stop tab 38 passes under the side wall 61a, it may enter the window 64 where it may freely travel.

As best seen in FIGS. 4A and 4B, the stop tab 38 and window 64 cooperate to allow the shield 60 to slidably move in relation to the body 20, but substantially define the limits of their relative movement. The shield 60 may slide proximally and distally until the stop tab 38 abuts a distal edge 68 and a proximal edge 66 of the window 64, respectively. Specifically, when the stop tab 38 engages the distal edge 68 of the window 64, as shown in FIG. 4A, the shield 60 is in the retracted or unguarded position. When the stop tab 38 engages the proximal edge 66 of the window 64, as shown in FIG. 4B, the shield is in the extended or guarded position.

While the stop tab 38 and window 64 cooperate to limit the movement of the shield 60, the catches 48, 76, and the cooperating detents 71 and detent pockets 40, 42 on the shield 60 and body 20 also cooperate to hold the shield 60 either in the retracted position and/or in the extended position. During assembly, the latch members 74 may be deflected radially outwardly to avoid contact between the catches 76 thereon and the mating catches 48 on the body 20. Similarly, the detent arms 70 may be deflected radially outwardly such that the detents 71 do not engage the distal detent pockets 42 while the shield 60 is directed to the retracted position.

As best seen in FIG. 1, once the shield 60 is fully retracted, the latch members 74 and the detent arms 70 are released, whereupon they resiliently return inward such that the catches 76 on the latch members 74 engage the mating catches 48 on the body 20, and the detents 71 engage the proximal detent pockets 40. In the retracted position, the stop tab 38 also abuts the distal edge 68 of the window 64, thereby preventing further proximal movement of the shield 60. The sloping distal edges 71a of the detents 71 engage the sloping distal edges 40a of the proximal detent pockets 40 on the body 20, thereby assisting the cooperating catches 48, 76 in preventing the shield 60 from moving distally. However, the frictional resistance between the sloping distal edges 71a, 40a of the detents 71 and the proximal detent pockets 40 may be overcome by a distal force, such as that provided by the spring mechanism 80 when the catches 48, 76 are released, as described further below. In addition, the slope of the sloping edges 40a, 42a may be adjusted to increase or decrease the frictional resistance, for example, to slow the shield 60 down when it initially advances from the retracted position.

Turning to FIGS. 1 and 5A–5C, once assembled, the passive needle guard 10 is ready to receive a cartridge, such as a conventional unit dose pre-filled syringe 90. The syringe 90 is preferably pre-assembled within the passive needle guard 10 before being furnished to a user, for example, at the time of manufacturing the passive needle guard 10. Alternatively, the user may be able to insert the syringe 90 into the passive needle guard 10 themselves if care is taken not to activate the shield 60 during assembly.

The preferred cartridge is a pre-filled syringe 90 that generally has a substantially smooth-walled cylindrical barrel 92 (see FIG. 1), a distal end or hub 94 including a hypodermic needle 95, a needle cover or cap (not shown), a proximal end 93 having a flange 96 (see FIG. 1), and a plunger 98. The flange 96 generally includes a flat edge 96a, possibly in a predetermined orientation with a label or graduation marks 92a on the barrel 92 of the pre-filled syringe 90. The flange 96 may have a sufficiently large width to provide a finger grip for the syringe 90, or may simply be a small lip to facilitate manufacturing, for example, on a filling line.

Although the syringe 90 shown is the preferred medication delivery system that may be used with a passive needle guard in accordance with the present invention, it will be appreciated that the passive needle guard 10 may be modified for use with other pre-filled or unit dose delivery systems, and that the term cartridge may include other such known systems. For example, the finger grip 50 on the proximal end 22 of the body 20 may be replaced with a plunger and plug assembly (not shown), such as that disclosed in U.S. Pat. No. 5,624,400, issued to Firth et al., the disclosure of which is expressly incorporated herein by reference. In addition, the collar 32 on the distal end 24 of the body 20 may be replaced with a double-ended needle cannula, such as that disclosed in the Firth et al. patent.

The distal end or hub 94 of the syringe 90 is inserted into the recess 51 of the finger grip 50 and the open proximal end 22 of the body 20 until it enters the cavity 26 and progresses distally towards the distal end 24 of the body 20. Once fully encapsulated, the distal end 94 of the syringe 90 may simply abut the distal end 24 of the body 20, or alternatively the distal end 94 may partially enter the opening 34 and engage the collar 32, thereby providing additional protection from lateral movement of the syringe 90.

Before the syringe 90 is inserted into the body 20 or before the flange 96 contacts the latch members 74, the latch members 74 may be deflected radially outward, while securing the shield 60 in the retracted position, for example, manually or in a jig or other mechanism. Thus, any contact between the latch members 74 and the syringe 90 may be avoided until the flange 96 passes the tips 78 of the latch members 74 and enters the recess 51 of the finger grip 50. The latch members 74 may then be released such that the catches 76 again engage the mating catches 48 on the body 20.

Alternatively, the syringe 90 may be inserted into the body 20 while the shield 60 is extended and the latch members 74 are consequently positioned distally away from the recess 51 into which the syringe 90 is to be inserted. Once the syringe 90 is fully inserted, the detents 71 may be disengaged from the distal detent pockets 42 and the shield 60 may be directed to the retracted position. In another alternative embodiment, an intermediate stop (not shown) may be provided to hold the shield 60 in a position between the extended and retracted positions, wherein the latch members 74 may be located distally away from the recess 51 into which the syringe 90 is to be inserted. Once the syringe 90 has been inserted, the shield may be directed to the retracted position where the catches 48, 76 may engage each other. The intermediate stop may then be disabled, for example, by being deflected or broken off, thereby preventing the intermediate stop from subsequently interfering with advancement of the shield 60 from the retracted position to the extended position.

As best seen in FIGS. 1 and 2C, as the syringe 90 becomes fully encapsulated within the cavity 26, the flange 96 of the syringe 90 contacts the locking detents 58 on the finger grip 50. The locking detents 58 have tapered proximal edges 58a, allowing the syringe 90 to be directed further distally, the flange 96 moving the locking detents 58 aside and entering the slot 57. The locking detents 58 have substantially blunt distal edges 58b that prevent the syringe 90 from being removed proximally from the slot 57, thereby substantially permanently locking the syringe 90 into the body 20, and preventing axial (i.e. proximal and/or distal) movement of the syringe 90 within the passive needle guard 10.

Returning to FIGS. 1 and 5A–5C, once the syringe 90 is locked into the passive needle guard 10 (the finger grip and locking mechanism are absent from FIGS. 5A–5C for simplification), the needle 95 and its cover (not shown) extend through the opening 34 on the collar 32 and the opening 65 on the distal end 63 of the shield 60. Preferably, the length of the shield 60 is substantially coextensive with the barrel 92 of the syringe 90, allowing the needle 95 to extend beyond the distal end 63 of the shield 60, but protecting the hub 94 of the pre-filled syringe 90.

The distal opening 65 in the shield 60 is generally circular and has a diameter larger than that of the needle 95 on the syringe 90, and may be provided with a variety of diameters, for example, larger than the syringe barrel 92 and/or hub 94, or configurations to facilitate use of the syringe 90. For example, the diameter of the opening 65 may be sufficiently large to accommodate a luer adapter (not shown) or other alternative distal tip to be provided on the syringe 90 or attached to the hub 94. Most preferably, the opening 65 has a diameter sufficiently small to minimize the risk of accidental sticks, for example, to prevent a finger from being directed into the shield 60 after use.

Turning to FIG. 5A, the syringe 90 encapsulated within the passive needle guard 10 may then be used in a conventional manner to deliver medication in the barrel 92. The needle cover (not shown) may be removed, the needle 95 inserted into the patient (not shown), and the medication delivered by depressing the plunger 98 distally. As may be seen from FIG. 1, the windows 64, 36 may facilitate observation of the barrel 92 of the syringe 90, allowing the user to monitor delivery of the medication therein.

Figure 14:
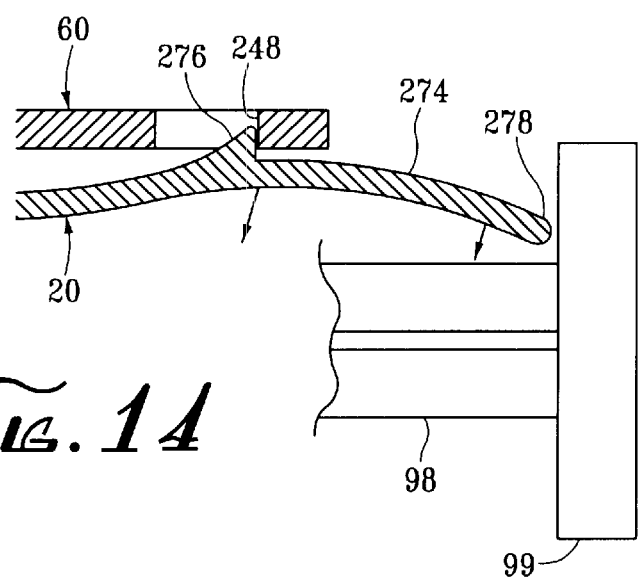
FIG. 14 is a cross-sectional side view of a passive needle guard, including a resilient latch member, a mating catch, and a thumb pad in accordance with another embodiment of the present invention.
Figure 6:
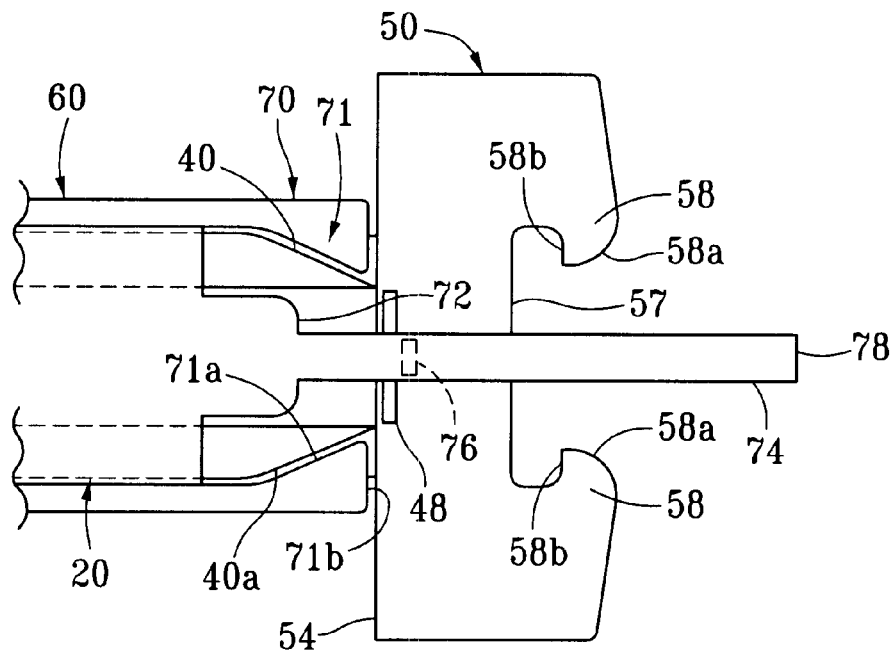
FIG. 6 is a side view of the proximal end of the passive needle guard of FIG. 1.

As shown in FIG. 5B, the plunger 98 may be depressed until the thumb pad 99 contacts the tips 78 of the latch members 74. As the plunger 98 is depressed further, the thumb pad 99 causes the latch members 74 to compress axially and thereby deflect radially outwardly until the catches 76 are disengaged from the mating catches 48 on the body 20. In an alternative embodiment, shown in FIG. 14, a resilient latch member 274 may be provided that extends proximally from the body 20, the latch member 274 including an outwardly disposed catch 276. The shield 60 may include a mating catch or pocket 248 for receiving the catch 276 on the latch member 274. Thus, when the plunger 98 is depressed, the latch member 274 may be deflectable radially inward for disengaging the catches 248, 276. In a second alternative embodiment, shown in FIG. 15, the body 20 may include an axially deflectable latch member 374 that has a ramped distal edge 372 opposite its proximal tip 378. The shield 60 may include a ramped proximal edge 349 on its proximal end 322 for engaging the ramped distal edge 372 of the latch member 374. The shield 60 and body include cooperating catches 376 and/or pockets 348 for engaging one another. When the plunger 98 is depressed distally, it may push the latch member 374 distally, thereby causing the ramped edges 349, 372 to slidably engage one another and deflect the proximal end 322 of the shield 60 radially outward until the catch 376 is disengaged from the pocket 348.

With the catches 48, 76 disengaged, the spring mechanism 80 biases the shield 60 distally, whereupon the shield 60 may automatically advance towards the extended position, shown in FIG. 5C. The latch members 74 merely slide along the body 20 as the shield 60 advances. Thus, the shield 60 may be automatically activated and advanced without requiring any action from the user other than depression of the plunger 98. Because of the predetermined location of the distal detent pockets 42, when the stop tab 38 reaches the proximal edge 66 of the window 64, the detents 71 substantially simultaneously enter the distal detent pockets 42, as may be seen in FIG. 4B. The blunt or oblique proximal edges 71b of the detents 71 engage the similarly shaped proximal edges 42b of the distal detent pockets 42, thereby preventing the shield 60 from being moved proximally. In an alternative embodiment, the body 20 may include pockets (not shown) for receiving the catches 76 on the latch members 74 when the shield 60 reaches the extended position, thereby further securing the shield 60 from proximal movement. Furthermore, because the stop tab 38 abuts the proximal edge 66 of the window 64, the shield 60 may not be moved further distally. Thus, the shield 60 is thereby substantially permanently locked in the extended position.

As best seen in FIG. 5C, as the shield 60 advances to the extended position, the distal end 63 of the shield 60 passes over the needle 95, covering the needle 95. Once the shield 60 is locked in the extended position, the needle 95 may no longer be accessible, thereby substantially eliminating the risk of accidental sticks, and preventing reuse of the syringe 90. The guard 10 and syringe 90 may then be disposed of in a conventional manner.

A useful feature of the passive needle guard is that the latch members 74 and/or the plunger 98 have predetermined relative lengths to activate the shield 60 at a desired time during the plunger stroke. For example, it may be desirable to activate the shield 60 early in the stroke such that the shield 60 is activated and advanced into contact with the patient's skin. Upon removal of the needle from the patient, the shield 60 simply slides completely to the extended position, automatically covering the needle 95 as it is withdrawn from the patient. Alternatively, the latch members 74 and/or plunger 98 may be configured to activate the shield 60 only upon complete depression of the plunger 98. In a further alternative, the plunger 98 may include a radial portion, such as a tab or an annular rib (not shown), at an intermediate location thereon. The radial portion may engage and deflect the latch members 75 during depression of the plunger 98, similar to the thumb pad 99 described above.

Turning to FIGS. 7A–11E, a second preferred embodiment of a passive needle guard 110 is shown that includes a body 120, a shield 160, and a spring mechanism 180, similar to the previous embodiment. As best seen in FIGS. 10A–10E, the body 120 has opposing side rails 128 defining two elongate openings or windows 136 and a cavity 126 extending between its proximal and distal ends 122, 124. Stop tabs 138 are molded on the distal end 124 of the body 120, preferably on two cantilever members 139 on opposite sides of the distal end 124. Catches or tabs 148 are molded on the proximal end 122 of the body 120.

A finger grip 150 is molded on the proximal end 122 of the body 120 that includes a pair of wing-like members or flanges 152 generally defining a "T" shape. A plurality of locking detents 158 partially defining an aperture or slot 157 are formed in lateral surfaces 155 of the finger grip 150. In addition, the finger grip 150 includes a pair of axial flanges 159 that extend distally from finger ledges 154. The axial flanges 159 are spaced apart from the side rails 128, and the finger ledges 154 have apertures 153 therethrough between the axial flanges 159 and the side rails 128.

A set of proximal detent pockets 140 is provided adjacent the finger grip 150, and a set of distal detent pockets 142 is provided at a more distal location on the body 120. Preferably, the proximal detent pockets 140 have sloping distal edges 140a and substantially blunt proximal edges 140b, and the distal detent pockets 142 have substantially blunt proximal edges 142b, similar to the embodiment described above.

Turning to FIGS. 11A–11E, the shield 160 is a tubular member adapted to slidably fit on the body 120 that includes four side walls 161a, 161b, an open proximal end 162, and an open distal end 163. Assembly tabs 172 with sloping or ramped interior surfaces 173 are molded into and extend proximally from the side walls 161a. At least one wall 161a, and preferably the two opposite walls 161a, include an elongate opening or window 164 therethrough to facilitate observation of a syringe received in the body 120, and also to provide a traveling slot for the stop tabs 138 on the body 120.

One or more latch members or fingers 174 extend proximally from the shield 160, preferably molded to each of the side walls 161b. Each latch member 174 includes an inwardly disposed catch or tab 176 located on an intermediate portion of the latch member 174 between the assembly tab 172 and a tip 178 of the latch member 174.

A plurality of detent arms 170 and a plurality of detents 171 are molded directly to the side walls 161b. The detents 171 preferably have shapes corresponding substantially to the shapes of the detent pockets 140, 142 in the body 120. Distal edges 171a of the detents 171 are preferably ramped to facilitate slidable engagement with the distal surfaces 140a of the proximal detent pockets 140. Proximal edges 171b of the detents 171 are substantially blunt for positively engaging the proximal edges 142b of the distal detent pockets 142 and locking the shield 160 in an extended position.

Turning to FIG. 7D, the spring mechanism 180 preferably includes a compression spring 182 that is disposed between the body 120 and the shield 60 to bias the shield 160 towards an extended position. The body 120 includes a substantially blunt distal surface 125 and the shield 160 includes a substantially blunt inner collar 167. The spring 182 may be positioned concentrically within the shield 160 such that respective ends of the spring 182 engage the distal surface 125 and the inner collar 167. Thus, the body 120 and shield 160 together at least partially define an annular space 184 within which the compression spring 182 may be compressed when the shield 160 is in a retracted position (shown in FIGS. 7A and 7B).

The passive needle guard 110 is pre-assembled similar to the embodiment described above, such that the shield 160 is disposed in a retracted position, as shown in FIGS. 7A–7D. In the retracted position, the latch members 174 extend through the corresponding apertures 153 in the finger grip 150, and the shield 160 passes freely between the axial flanges 159 on the finger grip 150 and the side rails 128 on the body 120. The catches 176 on the latch members 174 engage the mating catches 148 on the body, as best seen in FIG. 7C, thereby restraining the shield 160 in the retracted position. In addition, as best seen in FIG. 7A, the stop tabs 138 abut the distal edge 168 of the windows 164 and the detents 171 are received in the proximal detent pockets 140 in the retracted position.

A syringe 90, such as a pre-filled unit dose syringe, may be inserted axially into the body 120 through the open proximal end 22 until the barrel 92 is fully received in the cavity 126. A flange 96 on the syringe 90 may be received in the slot 157 defined by the locking detents 158, thereby substantially permanently locking the syringe 90 within the body 120. When the syringe 90 is inserted into the body 120, the latch members 174 may be deflected radially outwardly (not shown) while restraining the shield 160 in the retracted position to avoid contact between the flange 96 on the syringe 90 and the latch member 174. Alternatively, the syringe 90 may be inserted into the body 120 before the shield 160 is attached to the body 120 or before the shield 160 is directed to the retracted position to prevent accidental activation of the shield 160 during insertion of the syringe 90.

As described above, the passive needle guard 110 and syringe 90 may then be used to inject medication in the syringe 90 into a patient (not shown). A needle cover (not shown) may be removed from the needle 95, and the needle 95 inserted into the patient. Medication may then be delivered by directing the plunger 98 distally with the user's thumb until the thumb pad 99 contacts the tips 178 of the latch members 174. As the plunger 98 is depressed further, the thumb pad 99 causes the latch members 174 to compress axially and thereby deflect radially outwardly until the catches 176 are disengaged from the mating catches 148 on the body 120. With the catches 148, 176 disengaged, the spring mechanism 180 automatically advances the shield 160 distally towards the extended position, as shown in FIGS. 8A and 8B. The latch members 174 move distally through the apertures 153 in the finger grip 150 and slide along the body 120 as the shield 160 advances.

As best seen in FIGS. 9A and 9B, when the needle 95 is withdrawn from the patient, the shield 160 may advance fully to the extended position such that the shield 160 passes over and substantially covers the needle 95. In the extended position, the detents 171 are received in the distal detent pockets 142, thereby preventing subsequent proximal movement of the shield 160. The stop tabs 138 also abut the proximal edges 166 of the windows 164, thereby preventing further distal movement of the shield 160. Thus, the shield 160 is substantially permanently locked in the extended position, thereby preventing reuse of the syringe 90 and/or facilitating safe disposal of the passive needle guard 110 and syringe 90. In the extended position, the spring 182 may remain slightly compressed to provide a distal force that may ensure that the shield 160 is fully advanced and the detents 171 are received in the distal detent pockets 142.

A useful feature of this embodiment is the axial flanges 159 that extend from the finger grip 150. When a user grasps the finger grip 150, they generally place their fingers on the finger ledges 154. The axial flanges 159 prevent the fingers on the finger ledges 154 from contacting the shield 160. Otherwise, the user's fingers may interfere with the automatic movement of the shield 160 when the catches 148, 176 are disengaged.

Alternatively, it may be useful to eliminate the axial flanges 159 and allow the user to engage the shield 160 with their fingers, for example, when the user wants to manually augment or control the speed with which the shield 160 extends once it is activated. Alternatively, the axial flanges 159 may be sufficiently flexible, that the user may be able to deflect them slightly radially inward to contact the shield 160 and slow its advancement. Slowing the speed of activation may minimize discomfort or fear, particularly when dealing with younger patients. In addition, it may prevent abrupt extension of the shield 160, which may interfere with an injection made subcutaneously at an extreme angle.

In further alternatives, additional elements may be provided on the body 120 and/or shield 160 to slow advancement of the shield 160 from its initial activation in the retracted position, but allow free advancement as the shield 160 approaches the extended position. For example, a frictional material (not shown) may be applied to one or more contact surfaces between the body 120 and shield 160 that may increase the frictional resistance in the retracted position. An adhesive tape or viscous material may be provided that peels off of, is cut or torn, or otherwise separates from the body 120 and/or shield 160 after partial advancement of the shield 160. One or more "speed bumps" or similar protruding structures (not shown) may be molded into or otherwise provided on the body 120 and/or shield 160 that may be contacted when the shield 160 is in or close to the retracted position. A feature on one of the body 120 or shield 160 may travel through a corresponding tortuous feature on the other of the body 120 or shield 160 to slow the shield 160 down initially. In a further alternative, a spring or cushioned pad (not shown) may be provided on the distal end of the shield 160 that may soften the force with which the shield 160 contacts the patient as it is advanced.

Turning to FIGS. 16A–16C, a method for performing an injection using a passive needle guard 110, such as that just described, is shown. Unlike the previous embodiments, which generally discuss a shield advancing over a needle, this method involves holding a shield 160 of the guard 110 substantially stationary such that a body 120 of the guard 110 may be automatically and/or controllably directed proximally to retract a needle 95 within the shield 160. The body 120 and shield 160 are slidably attached to each other, similar to the previous embodiments. The guard 110 includes a spring mechanism 180, similar to the previous embodiments, for biasing the body 120 towards a position wherein the shield 160 substantially covers the needle 95.

Generally, the passive needle guard 110 may be provided with a syringe 90 received therein, as shown in FIG. 7A. As best seen in FIG. 16A, a needle cover (not shown) may be removed from the needle 95, and the needle 95 may be inserted into a patient's skin 100. A user may grasp distal finger grips 250, or otherwise grip an outer surface of the shield 160. Thus, the shield 160 may be grasped to hold the passive needle guard 110 substantially stationary with respect to the skin 100 during the injection.

To deliver medication from the syringe 90, the user may grip the finger grips 250 and apply a distal force on the plunger 98, preferably until thumb pad 99 engages latch members 174 extending from the passive needle guard 110. As the plunger 98 is depressed further, the thumb pad 99 causes the latch members 174 to compress axially and thereby deflect radially outwardly until the catches 176 (not shown in FIGS. 16A–16C) are disengaged from the mating catches 148 (also not shown) on the body 120. With the catches 148, 176 disengaged, the spring mechanism 180 automatically biases the body 120 towards a retracted position, shown in FIG. 16C.

Once the catches 148, 176 are disengaged, the user may gradually remove the distal force applied to the plunger 98, allowing a controlled retraction of the body 120 to the retracted position. As the body 120 retracts to the retracted position, the shield 160 remains substantially stationary with respect to the patient's skin 100, and the needle 95 may be withdrawn from the patient and into the shield 160, as shown in FIGS. 16B and 16C. Once in the fully retracted position, cooperating detents 171, 142 on the shield 160 and body 120 engage one another to substantially and permanently locking the shield 160 over the needle 95. Thus, the user may hold the distal finger grips 250 to hold the shield a predetermined distance way from the patient's skin 100, thereby avoiding any sudden contact between the shield 160 and the patient's skin 100 when the catches 148, 176 are disengaged.

Alternatively, as shown in FIGS. 17A–17C, the user may hold the passive needle guard 110 using finger grips 150, which extend from the body 120. The user may grip the finger grips 150, insert the needle 95 into the patient's skin 100, and inject medication by applying a distal force to the plunger 98 until the thumb pad engages a latch member 174 extending from the passive needle guard 110. As described above, further depression of the plunger 98 deflects the latch member 174 to disengage the cooperating catches 176, and releases the shield 160. The shield 160 may then automatically advance into contact with the patient's skin 100, as shown in FIG. 16B. The plunger 98 may be further advanced to complete the injection. Preferably, because the spring 182 is not fully expanded, the body 120 remains biased to retract with respect to the shield 160 towards the retracted position.

At this point, the user may gradually remove the distal force applied to the plunger 98, allowing controlled retraction of the body 120 to the retracted position, as shown in FIG. 17C. Once the body 120 retracts to the retracted position, the cooperating detents 171, 142 may engage one another to substantially and permanently lock the shield 160 over the needle 95, similar to the embodiment discussed above.

Turning to FIGS. 18A–18G, another preferred embodiment of a passive needle guard 410 is shown that may facilitate retraction of a body 420 containing a syringe 90 with respect to a shield 460. Generally, as best seen in FIGS. 18A and 18B, the guard 410 includes body 420, shield 460, and a spring mechanism (not shown), similar to the previous embodiments. The body 420 includes a cavity 426 extending between proximal and distal ends 422, 424 for receiving a syringe 90. Stop tabs 438 are molded on the distal end 424 of the body 420, preferably on cantilever members 439 on opposite sides of the distal end 424. A plurality of locking detents 458 partially defining an aperture or slot 457 are formed in lateral surfaces 455 on the proximal end 422. A set of proximal detent pockets 440 is provided adjacent the proximal end 422, and a set of distal detent pockets 442 is provided at a more distal location on the body 420, all similar to the previous embodiments.

The shield 460 is a generally tubular member adapted to slidably fit on the body 420 that includes an open proximal end 462, and an open distal end 463. At least one wall 461*a*, and preferably two opposite walls 461*a*, include an elongate opening or window 464 therethrough to facilitate observation of the syringe 90 received in the body 420, and also to provide a traveling slot for the stop tabs 438 on the body 420. A plurality of detent arms 470 and a plurality of detents 471 are molded directly to the side walls 461*b*. The detents 471 preferably have shapes corresponding substantially to the shapes of the detent pockets 440, 442 in the body 420, and cooperate similar to the embodiments described above. The shield 460 also includes a pair of finger grips 450 that extend substantially transversely outward from the shield 460.

With particular reference to FIGS. 18C–18G, a pair of latch members 474 extend proximally from the shield 460, preferably molded to each of the side walls 461*b*. Each latch member 474 includes a pair of catches or tabs 478 located on an intermediate portion of the latch member 474. Preferably, the tabs 478 include tapered proximal edges 478*a* and substantially blunt distal edges 478*b*. Mating catches, in the form of slotted apertures 448, are provided on the proximal end 422 of the body 420 for cooperating with the catches 478 on the respective latch members 474. As best seen in FIGS. 18E and 18F, the apertures include a relative wide region 448*a* and a relatively narrow region 448*b*, thereby defining catch surface 449.

The apertures 448 may be provided in a protective housing 427 on the proximal end 422 of the body 420, as shown in FIGS. 18A–18C. Preferably, the housing 427 is molded to the body 420 and includes the locking detents 458. Thus, the housing 427 may be similar to the finger grips described with respect to the embodiments above, although possibly with a smaller profile.

During assembly of the body 420 and shield 460, the tapered proximal edges 478*a* of the latch member 474 may facilitate insertion of the latch member 474 through the aperture 448, as will be appreciated by those skilled in the art. The blunt distal edges 478*b* of the latch member 474 may enhance engagement with the catch surfaces 449, i.e., to prevent relative movement of the body 420 and shield 460, as described below.

Returning to FIGS. 18A–18C, the syringe 90 includes a customized plunger 198 that includes an intermediate trigger flange 197 distal to thumb pad 199, although a conventional plunger (not shown) may also be provided). Preferably, the trigger flange 197 is molded to the plunger 198, and includes an annular proximal portion 197*a* that has a diameter smaller than an annular distal portion 197*b*. Thus, the trigger flange 197 includes one or more pockets 197*c* for receiving a tip 476 of the latch member 474 on the shield 460, as described below.

Before use of the guard 410, e.g. during manufacturing, the body 420, shield 460 and spring mechanism (not shown) are assembled until as shown in FIGS. 18A and 18B. In the assembled configuration, the catches 478 on the latch members 474 engage the mating catches 449 on the body 420. Specifically, as best seen in FIGS. 18E and 18G, the blunt distal edges 478*b* of the catches 478 abut the catch surfaces 449 defined by the apertures 448. Returning to FIGS. 18A and 18B, the syringe 90 may be encapsulated in the body 420, e.g., during manufacturing or prior to use, similar to the embodiments described above. Preferably, the syringe 90 is inserted into the open proximal end 422 of the body 420 and into the cavity 426 until a flange 96 on the syringe 90 is received in the slot 457 defined by locking detents 458, thereby locking the syringe 90 into the body 420.

The guard 410 may then be used, similar to the embodiments described above, to inject medication within the syringe 90 into a patient. The needle 95 is inserted into a patient's skin (not shown), while the user holds the finger grips 450 (e.g., with their index and middle fingers) and thumb pad 199 (e.g., with their thumb). Distal force is applied to the thumb pad 199, thereby depressing the plunger 198 and injecting medication within the syringe 90 through the needle 95. The plunger 98 is depressed until the tips 476 of the latch members 474 engage the pocket 197*c* of the trigger flange 197. As the plunger 198 is depressed further, the trigger flange 197 causes the latch members 474 to compress axially and thereby deflect radially outwardly, as indicated by arrow 480 (representing the distal or depression force) and arrow 482 (representing the deflection outward of the latch member 474).

As best seen in FIGS. 18E–18G, as the latch members 474 are deflected radially outward from a relaxed position (FIG. 18E) to a deflected position (FIG. 18F), the catches 478 are disengaged from the catch surfaces 449. This releases the body 420 and shield 460 and allows them to move relative to one another. Similar to the previous embodiments, because of the spring mechanism (not shown), the body 420 is biased to retract proximally, since the shield 460 is held stationary by the finger grips 450. As the user withdraws the distal force from the thumb pad 199, the body 420 may move proximally until the needle 95 is withdrawn from the patient and into the shield 460. When the plunger 198 is finally released, the body 420 fully retracts to a retracted position, whereupon the cooperating detents 442, 471 on the body 420 and shield 460 engage one another to lock the body 420 in the retracted position, similar to the embodiments described above.

Turning to FIGS. 19A–19C, another embodiment of a passive needle guard 510 is shown that includes a body 520, a shield 560, and a spring mechanism (not shown), similar to the previous embodiments. The body 520 includes a cavity 526 for receiving a syringe 90, and a plurality of locking detents 558 for engaging a flange 96 on the syringe 90. The shield 560 includes a pair of finger grips 550, similar to the previous embodiment. The body 520 and shield 560 include cooperating detents 540, 542, 571 for holding the body 520 in extended and retracted positions.

The shield 560 also includes a pair of latch members 574 including a pair of catches 578. Mating catches, namely slotted apertures 548, are provided on the proximal end 522 of the body 520 for cooperating with the catches 578 on the respective latch members 574. Preferably, each latch member 574 includes an angled tip portion 576, as best seen in FIG. 19C. The angled portion 576 of each latch member 574 extends substantially transversely outward at an acute angle, e.g., between about thirty and sixty (30–60) degrees, thereby defining an angled surface 576a. The syringe 90 includes a plunger 298 that may include a trigger flange 297. The trigger flange 297 may have an angled outer edge 297a or a substantially blunt outer edge (not shown) for engaging the angled surfaces 576a of the latch members 574.

This embodiment operates substantially similarly to the previous embodiment, except that the tip portions 576 of the latch members 574 are deflected radially outward to disengage the catches 578, rather than being compressed. Thus, when the plunger 98 is depressed, the trigger flange 297 engages and deflects the angled surfaces 576a, deflecting the latch members 574 outward until the catches 578 disengage catch surfaces (not shown) of apertures 548, releasing the body 520 and shield 560. Thus, the body 520 may automatically and/or controllably be retracted to withdraw the needle 95 into the shield 560, as described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for performing an injection using a passive needle guard including a body having a medicine cartridge therein comprising one of a syringe, ampoule or vial for containing medicine, and a shield slidably attached to the body, the body retained by cooperating catches on the body and the shield in a first position wherein the needle is exposed, the body being biased to retract with respect to the shield towards a second retracted position for covering a needle extending from the cartridge, the method comprising:
    inserting the needle into a patient's skin while holding the shield a predetermined distance therefrom;
    applying a distal force on a plunger communicating with the cartridge to inject medication into the patient until the plunger contacts a latch member extending from the passive needle guard;
    depressing the plunger further to deflect the latch member to disengage the cooperating catches, wherein the body becomes biased to move towards the retracted position; and
    releasing the distal force on the plunger, thereby retracting the body towards the retracted position, wherein the needle is substantially covered by the shield.

2. The method of claim 1, wherein the needle is withdrawn from the patient, as the body is retracted towards the retracted position.

3. The method of claim 1, wherein the needle is withdrawn into the shield as the body is retracted towards the retracted position.

4. The method of claim 1, wherein cooperating detents on the shield and the body engage one another when the body is retracted to the retracted position, thereby preventing subsequent movement of the body with respect to the shield.

5. The method of claim 1, wherein the latch member comprises a finger extending from the shield towards the plunger, the finger being compressed and thereby deflected radially outward to disengage a catch thereon from a mating catch on the body when the plunger is depressed.

6. The method of claim 5, wherein the plunger includes a radial portion for engaging a proximal tip of the finger as the plunger is depressed, the finger being compressed by the radial portion as the plunger is depressed to deflect the finger radially outward to disengage the catch thereon from the mating catch on the body.

7. The method of claim 1, wherein the distal force is applied to the plunger while holding finger grips on the shield, thereby holding the shield the predetermined distance from the patient's skin.

8. The method of claim 1, wherein the shield remains substantially stationary with respect to the patient's skin while medication is injected into the patient.

9. The method of claim 8, wherein the shield does not come in contact with the patient's skin while medication is injected into the patient.

10. A method for performing an injection using a passive needle guard including a body having a medicine cartridge therein comprising one of a syringe, ampoule or vial for containing medicine, and a shield slidably attached to the body, the shield being biased to move distally with respect to the body, the body and shield being retained by cooperating catches in a position wherein a needle extending from the cartridge is exposed, the method comprising:
    inserting the needle into a patient's skin while holding a portion of the body;
    applying a distal force on a plunger communicating with the cartridge to inject medication into the patient until the plunger engages a latch member extending from the passive needle guard;
    depressing the plunger further to deflect the latch member to disengage the cooperating catches, whereupon the shield advances automatically into contact with the patient's skin; and
    withdrawing the needle from the patient's skin, whereby the shield continues to advance distally with respect to the body until the needle is substantially contained within the shield.

11. The method of claim 10, wherein cooperating detents on the shield and the body engage one another when the needle is substantially contained within the shield, thereby preventing subsequent movement of the body with respect to the shield.

12. The method of claim 10, wherein the latch member comprises a finger extending from the shield towards the plunger, the finger being compressed and thereby deflected radially outward to disengage a catch thereon from a mating catch on the body when the plunger is depressed.

13. The method of claim 12, wherein the plunger includes a radial portion for engaging a proximal tip of the finger plunger as the plunger is depressed, the finger being compressed by the radial portion as the plunger is depressed to deflect the finger radially outward to disengage the catch thereon from the mating catch on the body.

14. A passive needle guard, comprising:
    a body having proximal and distal ends and a cavity therein for receiving a medicine cartridge comprising one of a syringe, ampoule or vial for containing medicine, and the cartridge having a distal tip for administering a medication from within the cartridge;
    a shield having proximal and distal ends, the shield slidably attached to the body, the body being biased to retract with respect to the shield from a first position wherein the distal tip of the cartridge is exposed towards a second retracted position for withdrawing the distal tip of the cartridge into the shield;

cooperating catches on the body and the shield for holding the body and shield in the extended position; and a latch member extending proximally from the proximal end of one of the shield and the body, the latch member being deflectable for disengaging the cooperating catches upon depression of a plunger coupled to the medicine cartridge, whereby the body may be retracted to the retracted position.

15. The passive needle guard of claim 14, further comprising a trigger flange extending radially outward from the plunger, the trigger flange configured for deflecting the latch member to disengage the cooperating catches upon depression of the plunger.

16. The passive needle guard of claim 15, wherein the trigger flange comprises a pocket for receiving a proximal tip of the latch member, whereby an intermediate portion of the latch member is deflected radially outward for disengaging the cooperating catches when the tip of the latch member is received in the pocket and the plunger is depressed distally.

17. The passive needle guard of claim 15, wherein the trigger flange is located at a predetermined position location on the plunger for disengaging the cooperating catches at an intermediate portion of the plunger stroke.

18. The passive needle guard of claim 15, wherein the latch member comprises a proximal tip surface that is angled radially outward, whereby, upon depression of the plunger, the trigger flange engages the surface to deflect the latch member radially outward to disengage the cooperating catches.

19. The passive needle guard of claim 15, wherein the trigger flange comprises a tapered distal edge, whereby, upon depression of the plunger, the tapered distal edge of the trigger flange engages the latch member to deflect the latch member radially outward to disengage the cooperating catches.

20. The passive needle guard of claim 14, further comprising one or more finger grips extending from the shield.

21. The passive needle guard of claim 14, wherein the body and shield comprises cooperating detents for substantially permanently the body in the retracted position.

22. The passive needle guard of claim 14, further comprising a medical cartridge received in the cavity such that a distal tip of the cartridge extends beyond the distal end of the body.

23. The passive needle guard of claim 22, wherein the distal tip of the cartridge comprises a needle.

24. The passive needle guard of claim 21, further comprising a locking mechanism on the proximal end of the body for locking the cartridge received within the cavity.

25. A method as in claim 1 wherein the medicine cartridge is a prefilled syringe.

26. A method as in claim 1 wherein the medicine cartridge is a unit dose syringe.

27. A method as in claim 14 wherein the medicine cartridge is a prefilled syringe.

28. A method as in claim 14 wherein the medicine cartridge is a unit dose syringe.

* * * * *

(12) EX PARTE REEXAMINATION CERTIFICATE (8481st)
United States Patent
Doyle

(10) Number: US 6,613,022 C1
(45) Certificate Issued: Aug. 23, 2011

(54) PASSIVE NEEDLE GUARD FOR SYRINGES

(75) Inventor: Mark Christopher Doyle, San Diego, CA (US)

(73) Assignee: Safety Syringes, Inc., Carlsbad, CA (US)

Reexamination Request:
No. 90/011,390, Dec. 16, 2010

Reexamination Certificate for:
Patent No.: 6,613,022
Issued: Sep. 2, 2003
Appl. No.: 09/724,657
Filed: Nov. 28, 2000

Related U.S. Application Data

(63) Continuation-in-part of application No. 09/566,224, filed on May 5, 2000, now Pat. No. 6,623,459.

(51) Int. Cl.
*A61M 5/32* (2006.01)

(52) U.S. Cl. .................................................. 604/192
(58) Field of Classification Search .................. 604/162
See application file for complete search history.

(56) References Cited

U.S. PATENT DOCUMENTS

| | | |
|---|---|---|
| 5,295,965 A | 3/1994 | Wilmot |
| 5,324,265 A | 6/1994 | Murray et al. |
| 5,376,080 A | 12/1994 | Petrussa |
| 6,186,980 B1 | 2/2001 | Brunel |
| 6,585,702 B1 | 7/2003 | Brunel |

*Primary Examiner*—Jeanne M Clark

(57) ABSTRACT

A passive needle guard includes a body having a cavity therein for receiving a syringe, and a shield. The body is slidable with respect to the shield between retracted and extended positions covering and exposing, respectively, a needle extending from the syringe, the body being biased towards the retracted position. Latch members extend from the shield that include catches for engaging mating catches on the body for holding the body in the extended position. During use, the needle extending from the syringe is inserted into a patient. A plunger is depressed to inject medication from the syringe, thereby deflecting the latch members to disengage the catches and release the body, whereupon the user may controllably retract the body to the retracted position. In the retracted position, cooperating detents on the shield and body engage one another, thereby substantially permanently covering the needle with the shield.

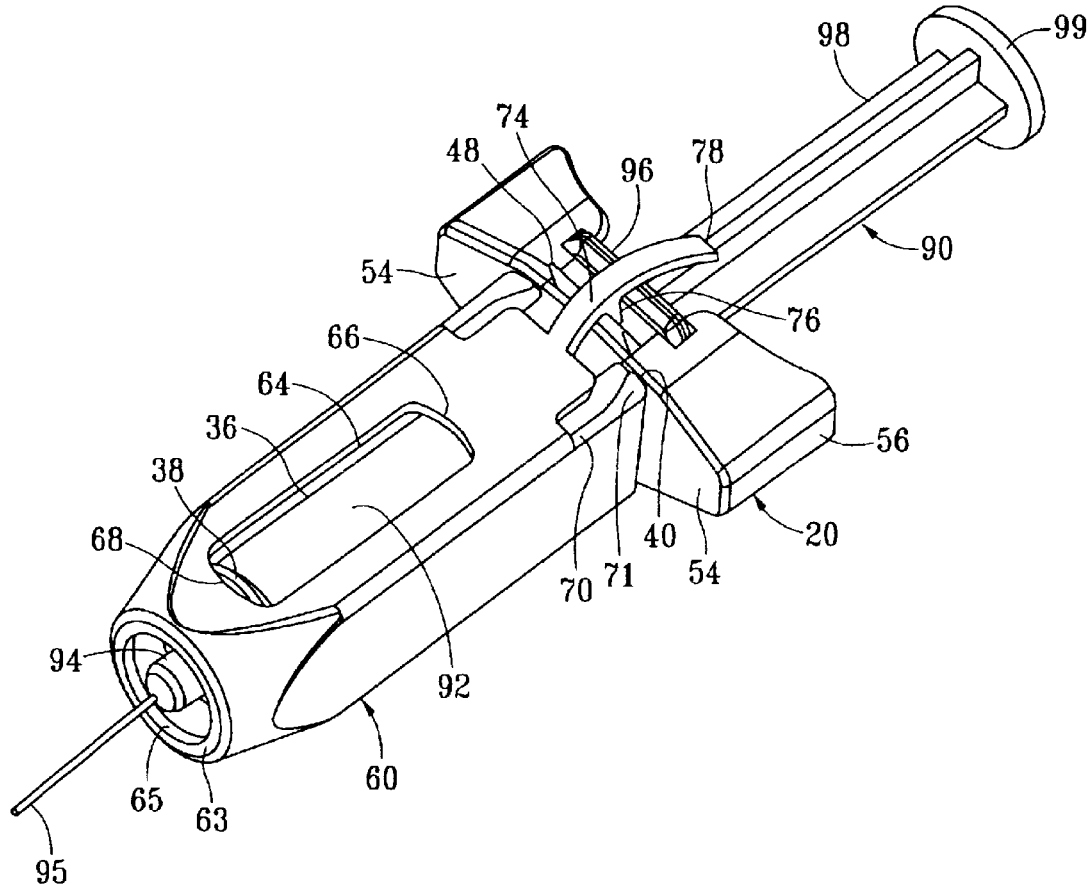

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 10, 13, 14 and 21 are determined to be patentable as amended.

Claims 2-9, 11, 12, 15-20 and 22-28, dependent on an amended claim, are determined to be patentable.

1. A method for performing an injection using a passive needle guard including a body having a medicine cartridge therein comprising one of a syringe, ampoule or vial for containing medicine *and having a plunger slidably received in the medicine cartridge*, and a shield slidably attached to the body, the body retained by cooperating catches on the body and the shield in a first position wherein the needle is exposed *beyond the shield*, the body being biased to retract with respect to the shield towards a second retracted position for covering a needle extending from the cartridge, the method comprising:

inserting the needle into a patient's skin while holding the shield a predetermined distance therefrom;

applying a distal force on [a] *the* plunger communicating with the cartridge [to inject] *and injecting* medication into the patient *from the medicine cartridge* until the plunger contacts a latch member extending from *the body or shield of* the passive needle guard;

depressing the plunger further *while injecting medication into the patient from the medicine cartridge* to deflect the latch member to disengage the cooperating catches, wherein the body becomes biased to move towards the retracted position; and releasing the distal force on the plunger, thereby retracting the body towards the retracted position, wherein the needle is substantially covered by the shield.

10. A method for performing an injection using a passive needle guard including a body having a medicine cartridge therein comprising one of a syringe, ampoule or vial for containing medicine *and having a plunger slidably received in the medicine cartridge*, and a shield slidably attached to the body, the shield being biased to move distally with respect to the body, the body and shield being retained by cooperating catches in a position wherein a needle extending from the cartridge is exposed *beyond the shield*, the method comprising:

inserting the needle into a patient's skin while holding a portion of the body;

applying a distal force on [a] *the* plunger communicating with the cartridge [to inject] *and injecting* medication into the patient *from the medicine cartridge* until the plunger engages a latch member extending from *the body or shield of* the passive needle guard;

depressing the plunger further *while injecting medication into the patient from the medicine cartridge* to deflect the latch member to disengage the cooperating catches, whereupon the shield advances automatically into contact with the patient's skin; and withdrawing the needle from the patient's skin, whereby the shield continues to advance distally with respect to the body until the needle is substantially contained within the shield.

13. The method of claim 12, wherein the plunger includes a radial portion for engaging a proximal tip of the finger [plunger] as the plunger is depressed, the finger being compressed by the radial portion as the plunger is depressed to deflect the finger radially outward to disengage the catch thereon from the mating catch on the body.

14. A passive needle guard, comprising:

a body having proximal and distal ends and a cavity therein for receiving a medicine cartridge comprising one of a syringe, ampoule or vial for containing medicine, and the cartridge having *a plunger slidably received therein and* a distal tip for administering a medication from within the cartridge;

a shield having proximal and distal ends, the shield slidably attached to the body, the body being biased to retract with respect to the shield from a first *extended* position wherein the distal tip of the cartridge is exposed *beyond the shield,* towards a second retracted position for withdrawing the distal tip of the cartridge into the shield;

cooperating catches on the body and the shield for holding the body and shield in the *first* extended position; and a latch member extending proximally from the proximal end of one of the shield and the body, the latch member being deflectable for disengaging the cooperating catches upon depression of [a] *the* plunger coupled to the medicine cartridge *during the plunger stroke to inject medicine from the medicine cartridge*, whereby the body may be retracted to the *second* retracted position.

21. The passive needle guard of claim 14, wherein the body and shield comprises cooperating detents for substantially *locking* permanently the body in the retracted position.

\* \* \* \* \*